(12) United States Patent
Harada

(10) Patent No.: US 11,564,555 B2
(45) Date of Patent: Jan. 31, 2023

(54) ENDOSCOPE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 230 days.

(21) Appl. No.: 16/826,283

(22) Filed: Mar. 22, 2020

(65) Prior Publication Data

US 2020/0221929 A1 Jul. 16, 2020

Related U.S. Application Data

(63) Continuation of application No. PCT/JP2018/035325, filed on Sep. 25, 2018.

(30) Foreign Application Priority Data

Sep. 28, 2017 (JP) .............................. JP2017-188594

(51) Int. Cl.
  *A61B 1/00* (2006.01)
  *A61B 1/005* (2006.01)

(52) U.S. Cl.
  CPC ...... *A61B 1/00087* (2013.01); *A61B 1/00002* (2013.01); *A61B 1/0055* (2013.01);
  (Continued)

(58) Field of Classification Search
  CPC .............. A61B 1/0087; A61B 1/00002; A61B 1/00066; A61B 1/0098; A61B 1/00101; A61B 1/00137; A61B 1/00147
  See application file for complete search history.

(56) References Cited

U.S. PATENT DOCUMENTS 5,707,344 A * 1/1998 Nakazawa ......... A61B 1/00066
  600/125
7,846,090 B2 * 12/2010 Pilvisto .............. A61B 1/00098
  600/149

(Continued)

FOREIGN PATENT DOCUMENTS

CN 104665753 6/2015
CN 105982635 10/2016

(Continued)

OTHER PUBLICATIONS

Office Action of Japan Counterpart Application, with English translation thereof, dated Apr. 5, 2021, pp. 1-8.

(Continued)

*Primary Examiner* — John P Leubecker
*Assistant Examiner* — Jae Woo
(74) *Attorney, Agent, or Firm* — JCIPRNET

(57) ABSTRACT

Provided is an endoscope that can easily perform the attachment and detachment work of a proximal end side of a wire without impairing the operability of an operating part.
The an endoscope includes an operating part (22) including an erection operating lever (20), an insertion part (24), an elevator (30), a wire (60) that is disposed to be inserted into a wire channel (62) to be movable forward and backward therethrough and is attachably and detachably coupled to the elevator (30) on a distal end side thereof, an opening part (94) that is provided at a proximal end of the wire channel (62) and delivers the proximal end side of the wire (60) to the outside of the operating part (22), a rotating member (96) that is disposed to be exposed to the outside of the operating part (22) and is configured to be rotatable around a rotational axis (96A) having a component in a direction orthogonal to a longitudinal direction of the operating part (22) depending on the operation of the erection operating lever (20), an engaged part (144) that is provided in the rotating member (Continued)

(96), and an engaging part (98) that is provided on the proximal end side of the wire (60) and is engageably and disengageably engageable with the engaged part (144).

12 Claims, 24 Drawing Sheets

(52) U.S. Cl.
CPC ........ *A61B 1/0057* (2013.01); *A61B 1/00066* (2013.01); *A61B 1/00098* (2013.01); *A61B 1/00101* (2013.01); *A61B 1/00137* (2013.01); *A61B 1/00147* (2013.01)

(56) References Cited

U.S. PATENT DOCUMENTS

| | | | | |
|---|---|---|---|---|
| 9,532,794 | B2* | 1/2017 | Jinno | A61B 34/70 |
| 9,610,129 | B2* | 4/2017 | Dejima | A61B 17/29 |
| 10,149,603 | B2* | 12/2018 | Iwasaka | A61B 1/00137 |
| 10,165,930 | B2* | 1/2019 | Tanaka | A61B 1/00098 |
| 10,219,679 | B2* | 3/2019 | Tanaka | A61B 1/00098 |
| 10,357,145 | B2* | 7/2019 | Fukushima | A61B 1/018 |
| 11,229,352 | B2* | 1/2022 | Ito | A61B 1/018 |
| 2005/0192475 | A1* | 9/2005 | Okada | A61B 1/0052 |
| | | | | 600/106 |
| 2015/0148598 | A1* | 5/2015 | Fukushima | A61B 1/00098 |
| | | | | 600/109 |
| 2016/0089125 | A1* | 3/2016 | Morimoto | A61B 1/00098 |
| | | | | 600/107 |
| 2016/0270635 | A1* | 9/2016 | Tanaka | A61B 1/00098 |
| 2019/0015172 | A1* | 1/2019 | Yamaya | A61B 90/03 |
| 2020/0214544 | A1* | 7/2020 | Harada | A61B 1/012 |
| 2020/0305691 | A1* | 10/2020 | Morimoto | A61B 8/12 |
| 2020/0315428 | A1* | 10/2020 | Harada | A61B 1/01 |
| 2020/0345210 | A1* | 11/2020 | Harada | A61B 1/00066 |
| 2020/0390316 | A1* | 12/2020 | Hosogoe | A61B 1/00101 |
| 2021/0169312 | A1* | 6/2021 | Morimoto | A61B 1/07 |
| 2022/0061631 | A1* | 3/2022 | Harada | A61B 1/0008 |

FOREIGN PATENT DOCUMENTS

| | | |
|---|---|---|
| EP | 1568305 | 8/2005 |
| EP | 1759626 | 3/2007 |
| EP | 2878253 | 6/2015 |
| JP | S59181126 | 10/1984 |
| JP | S62227312 | 10/1987 |
| JP | H045802 | 1/1992 |
| JP | H06315458 | 11/1994 |
| JP | H09238898 | 9/1997 |
| JP | 2003305002 | 10/2003 |
| JP | 2012081012 | 4/2012 |
| JP | 2013197765 | 9/2013 |
| WO | 2013099390 | 7/2013 |

OTHER PUBLICATIONS

"Search Report of Europe Counterpart Application", dated Nov. 12, 2020, p. 1-p. 7.

"Office Action of Japan Counterpart Application" with English translation thereof, dated Sep. 27, 2021, p. 1-p. 6.

Office Action of China Counterpart Application, with English translation thereof, dated Dec. 30, 2021, pp. 1-30.

"Office Action of Japan Counterpart Application" with English translation thereof, dated Mar. 24, 2022, p. 1-p. 6.

"International Search Report (Form PCT/ISA/210) of PCT/JP2018/035325," dated Nov. 13, 2018, with English translation thereof, pp. 1-3.

"International Preliminary Report on Patentability (Form PCT/IPEA/409) of PCT/JP2018/035325," completed on Oct. 8, 2019, with English translation thereof, pp. 1-7.

"Office Action of Europe Counterpart Application, Application No. 18863186.5", dated Jul. 19, 2022, p. 1-p. 5.

"Office Action of China Counterpart Application" with English translation thereof, dated Aug. 26, 2022, p. 1-p. 39.

* cited by examiner

ENDOSCOPE

CROSS-REFERENCE TO RELATED APPLICATIONS

The present application is a Continuation of PCT International Application No. PCT/JP2018/035325 filed on Sep. 25, 2018 claiming priority under 35 U.S.C § 119(a) to Japanese Patent Application No. 2017-188594 filed on Sep. 28, 2017. Each of the above applications is hereby expressly incorporated by reference, in its entirety, into the present application.

BACKGROUND OF THE INVENTION

1. Field of the Invention

The present invention relates to an endoscope, and particularly, to an endoscope including a forceps elevator that changes a delivery direction of a treatment tool to a distal end part of an insertion part.

2. Description of the Related Art

In endoscopes, various treatment tools are introduced from a treatment tool introduction port provided in a proximal operating part (hereinafter referred to as an "operating part"), and the treatment tools are delivered from a treatment tool delivery port opening to a distal end member of an insertion part to the outside and are used for treatment. For example, treatment tools, such as forceps or a contrast tube, are used in duodenoscopes, and treatment tools, such as a puncturing needle, are used in ultrasonic endoscopes. In such treatment tools, it is necessary to change a delivery direction of a treatment tool delivered from a treatment tool delivery port in order to treat a desired position within a subject. For this reason, the distal end member is provided with a forceps elevator (hereinafter also referred to as an "elevator"). Additionally, the operating part is provided with a treatment tool erection mechanism that changes the posture of the elevator between an erected position and a lodged position.

As the treatment tool erection mechanism, a wire pulling type mechanism to which a distal end part of a wire (also referred to as a forceps raising wire) is directly attached to the elevator is known (refer to JP1994-315458A (JP-H06-315458A)). This mechanism is a mechanism in which a proximal end side of the wire is coupled to an erection operating lever (also referred to as forceps raising lever) provided in the operating part, and the posture of the elevator is changed between the erected position and the lodged position by performing a push/pull operation of the wire by the erection operating lever, thereby rotating the elevator around a rotational movement shaft.

Specifically, the operating part of JP1994-315458A (JP-H06-315458A) is provided with a grip part for holding the operating part by hand and an angle knob. In this operating part, a wire opening part is provided below the grip part, a drive shaft opening part is provided in the grip part, a proximal end of the wire is delivered from a wire opening part, and a distal end of the drive shaft moved by the forceps raising lever is delivered from the drive shaft opening part. The distal end of the drive shaft and the proximal end of the wire are detachably coupled to a connection tool having a set screw.

Meanwhile, in a case where the endoscopes shown in JP1994-315458A (JP-H06-315458A) and EP1759626B are used for various kinds of examination or treatment, a body fluid adheres to the distal end member of the insertion part including the elevator and a guide tube through which the wire is inserted. Thus, after use, the endoscopes are subjected to cleaning and disinfection treatment, using a cleaning liquid and a disinfectant solution. In that case, the diameter of the guide tube is small and the wire is inserted through the guide tube. Therefore, in order to obtain a sufficient cleaning effect, substantial time and effort are taken for cleaning.

Thus, in the endoscope of JP1994-315458A (JP-H06-315458A), the cover, the elevator, and the wire, which cover the distal end member of the insertion part, are attachably and detachably provided, the cover, and the elevator, and the wire are detached, and the distal end member of the insertion part and the guide tube of the wire are cleaned.

Meanwhile, EP1759626B discloses an endoscope in which a proximal end of a cable cord is delivered from the proximal end of the control handle, and a collet is connected to a proximal end of the cable cord. The collet is fastened to a nut and moves in a forward-backward direction by the operating lever.

SUMMARY OF THE INVENTION

However, the endoscope of JP1994-315458A (JP-H06-315458A) has a configuration in which the connection tool, which connects the proximal end side of the wire to the erection operating lever side, is housed in a narrow interior of the operating part, and the set screw is rotated to connect the proximal end side of the wire to a connection part. Thus, there is a problem that the attachment and detachment work of the proximal end side of the wire with respect to the connection part becomes complicated. Additionally, in the endoscope of JP1994-315458A (JP-H06-315458A), in a case where an attempt to secure the internal space of the operating part is made in order to facilitate the attachment and detachment work of the proximal end side of the wire, The operating part is enlarged or complicated and the operability of the operating part is impaired.

Meanwhile, in the endoscope of EP1759626B, the cable cord is delivered to the outside of the control handle, and the distal end of the cable cord is attachably and detachably mounted to the collet and the nut. However, the attachment and detachment work is complicated.

The invention has been made in view of such circumstances, and an object thereof is to provide an endoscope that can easily perform the attachment and detachment work of a proximal end side of a wire without impairing the operability of an operating part.

In order to achieve the object of the invention, the endoscope of the invention comprises an operating part that is provided with an operating member; an insertion part that is provided on a distal end side of the operating part and is inserted into a subject; a forceps elevator (elevator) that is provided at a distal end part of the insertion part; an erection operating wire that is disposed to be inserted into a wire insertion passage formed from the operating part to the insertion part so as to be movable forward and backward and is attachably and detachably coupled to the forceps elevator (elevator) on a distal end side thereof; an opening part that is provided at a proximal end of the wire insertion passage and delivers a proximal end side of the erection operating wire to an outside of the operating part; a rotating member that is disposed to be exposed to the outside of the operating part and is configured to be rotatable around a rotational axis having a component in a direction orthogonal to a longitudinal direction of the operating part depending on the operation of the operating member; an engaged part that is provided in the rotating member; and an engaging part that is provided on the proximal end side of the erection operating wire and is engageably and disengageably engageable with the engaged part.

In one aspect of the invention, it is preferable to further comprise a locking member that is attachably and detachably mountable on the rotating member and is switchable between a locked position where release of an engaged state between the engaged part and the engaging part is prevented and an unlocked position where the release of the engaged state between the engaged part and the engaging part is allowed.

In one aspect of the invention, it is preferable that the rotating member has an engaging projection, and the locking member has an engaging groove with which the engaging projection attachably and detachably engages and which is switchable between a locked position where the engaging projection and the engaging groove engage with each other and an unlocked position where the engagement between the engaging projection and the engaging groove is released.

In one aspect of the invention, it is preferable the engaged part has a rotation restricting part that restricts relative rotation of the engaging part with respect to the engaged part.

In one aspect of the invention, it is preferable that the rotation restricting part has a D-cut rotation restricting surface that is formed in the engaged part.

In one aspect of the invention, it is preferable to further comprise a cap member that is attachably and detachably mountable on the rotating member and maintains an engaged state between the engaged part and the engaging part by abutting against the erection operating wire to apply a tension.

In one aspect of the invention, it is preferable that the rotating member has an engaging projection, and the cap member has an engaging groove with which the engaging projection attachably and detachably engages and which is switchable between a locked position where release of a mounted state between the rotating member and the cap member is prevented by engaging the engaging projection and the engaging groove with each other and an unlocked position where the release of the mounted state between the rotating member and the cap member is allowed by releasing the engagement between the engaging projection and the engaging groove.

In one aspect of the invention, it is preferable that the engaging part has an engaging piece provided on the proximal end side of the erection operating wire, and the engaged part has an engaging recess with which the engaging piece engages, and an engaging claw which is disposed at least on one side of both sides of the engaging recess and with which the erection operating wire engages.

In one aspect of the invention, it is preferable that the engaging part has an engaging piece provided on the proximal end side of the erection operating wire, and the engaged part has an engaging recess with which the engaging piece engages, a restricting part that restricts the engaging piece from slipping out in a direction parallel to the rotational axis from the engaging recess, and an opening part that is continuously connected to the engaging recess for attachably and detachably engaging the engaging piece with the engaging recess.

In one aspect of the invention, it is preferable to further comprise an engaging piece holding member that is provided on the proximal end side of the erection operating wire and holds the engaging piece, and it is preferable that the engaging piece is disposed at a position offset in a direction orthogonal to an axial direction of the erection operating wire from the erection operating wire.

According to the invention, the attachment and detachment work of a proximal end side of a wire can be easily performed without impairing the operability of an operating part.

DESCRIPTION OF THE PREFERRED EMBODIMENTS

Hereinafter, preferred embodiments of an endoscope according to the invention will be described with reference to the accompanying drawings.

Figure 1:
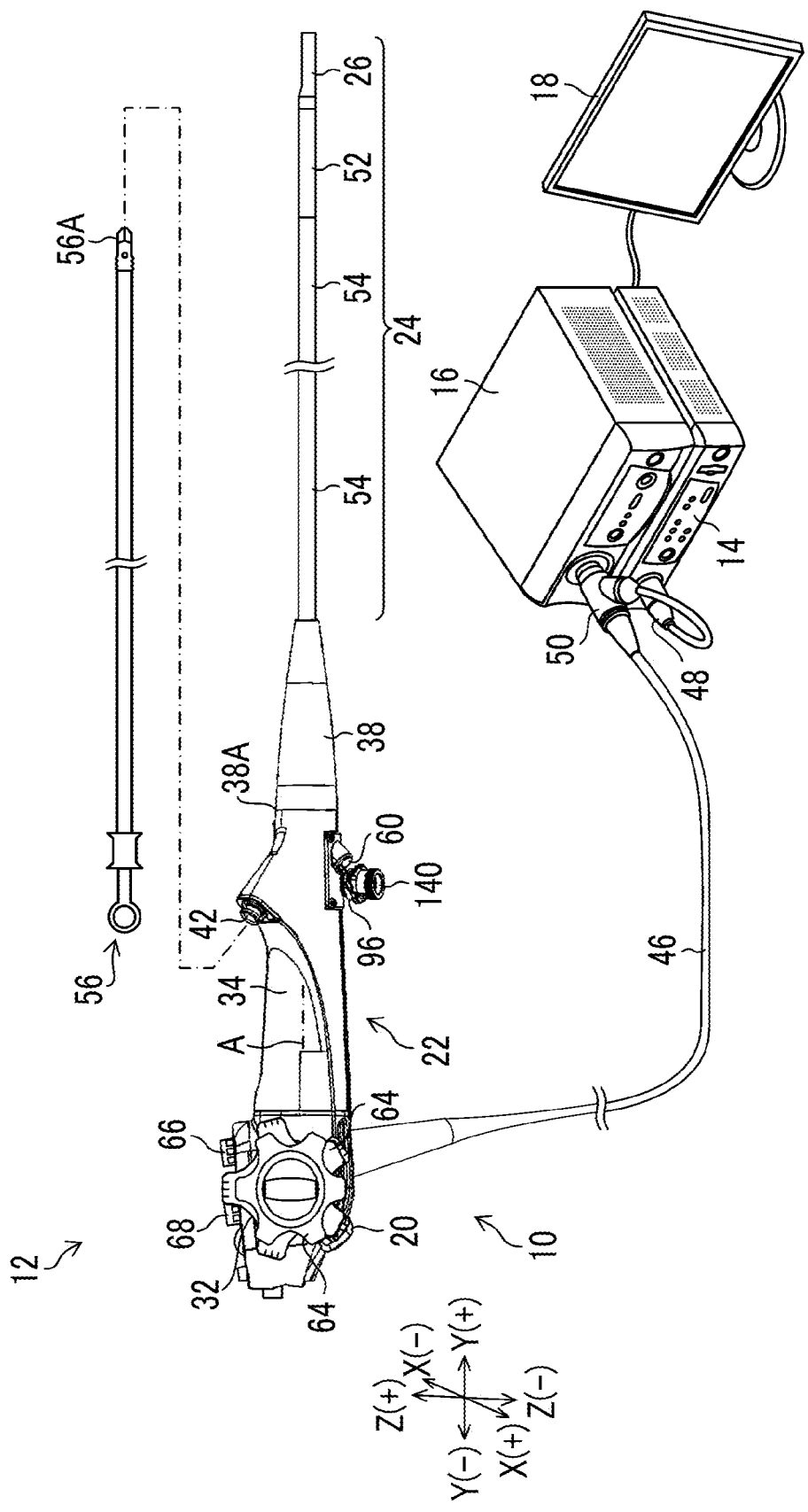
FIG. 1 is a configuration view of an endoscope system comprising an endoscope according to an embodiment.

FIG. 1 is a configuration view of an endoscope system 12 comprising an endoscope 10 according to an embodiment of the invention. The endoscope system 12 comprises the endoscope 10, a processor device 14, a light source device 16, and a display 18. In addition, a treatment tool 56 to be used in the endoscope system 12 is also illustrated in FIG. 1.

The endoscope 10 comprises an operating part 22 in which an erection operating lever 20 is provided, and an insertion part 24 that is provided on a distal end side of the operating part 22 and is inserted into a subject. The erection operating lever 20 is equivalent to an operating member of the invention.

Figure 2:
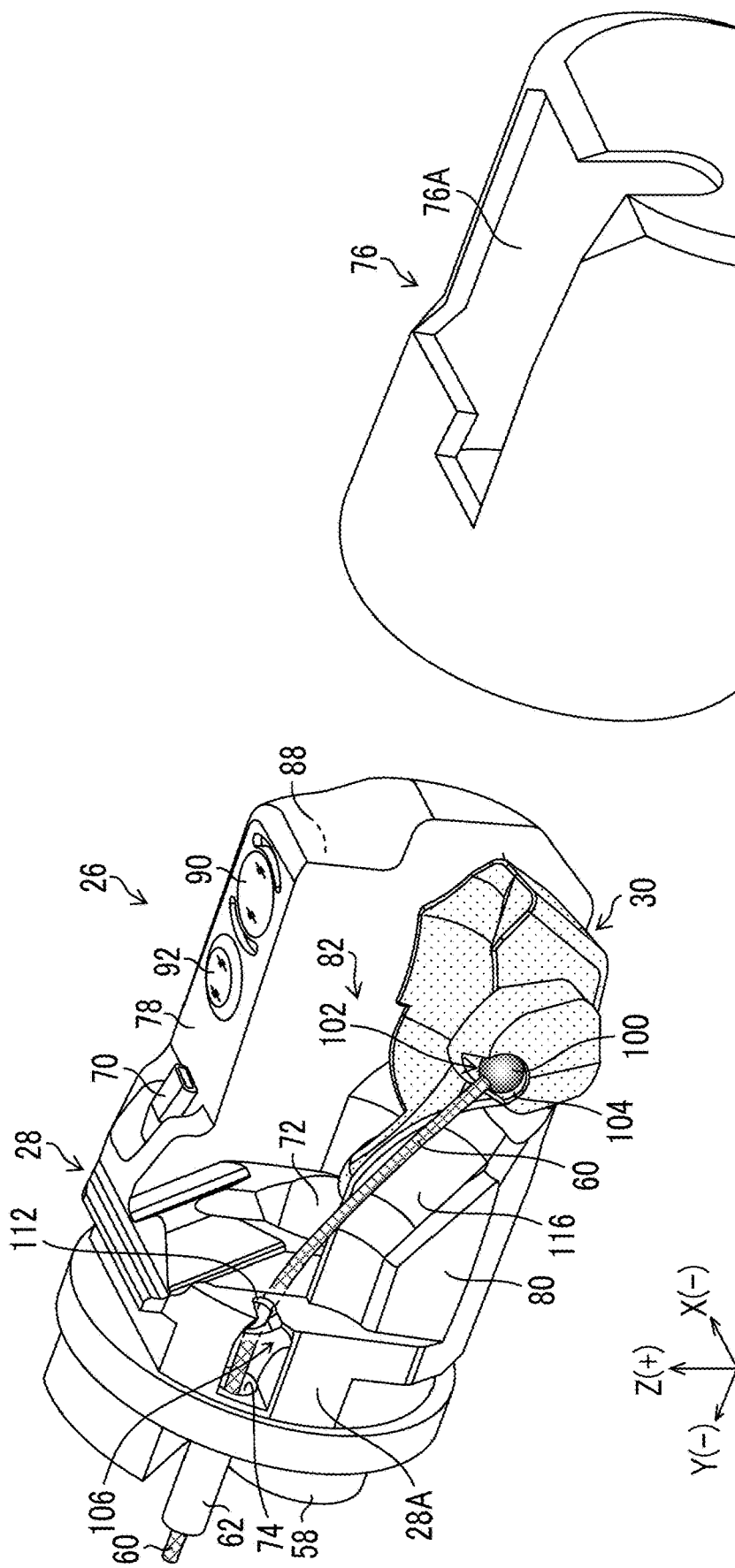
FIG. 2 is a perspective view of a distal end member where an elevator is located at a lodged position.
Figure 3:
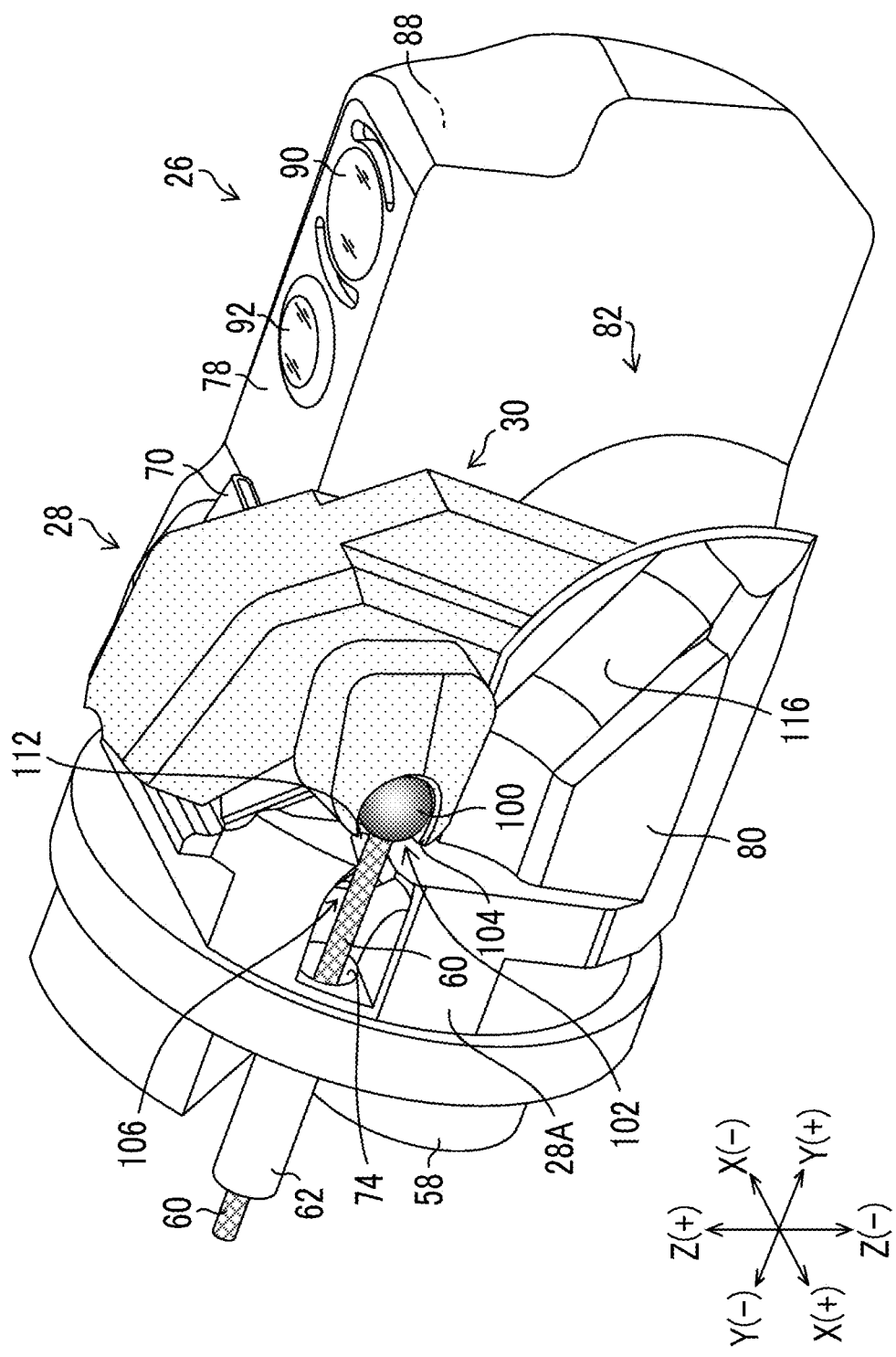
FIG. 3 is a perspective view of the distal end member where the elevator is located at an erected position.

Additionally, as illustrated in perspective views of FIGS. 2 and 3 illustrating the configuration of a distal end part 26 of the insertion part 24, a distal end part 26 of the insertion part 24 is provided with a distal end member 28, and the distal end member 28 is provided with an elevator 30 to be described below. FIG. 2 is a perspective view of the distal end member 28 where the elevator 30 is located at a lodged position, and FIG. 3 is a perspective view of the distal end member 28 where the elevator 30 is located at an erected position.

In addition, in the following description, an upward direction refers to a Z(+) direction of FIGS. 1 and 2, and a downward direction refers to a Z(−) direction of FIGS. 1 and 2. Additionally, a rightward direction refers to an X(+) direction of FIG. 2, and a leftward direction refers to an X(−) direction of FIG. 2. Moreover, a Y(+) direction of FIGS. 1 and 2 refers to a distal-end-side direction of the distal end member 28, and a Y(−) direction of FIGS. 1 and 2 refers to a proximal-end-side direction of the distal end member 28.

As illustrated in FIG. 1, the operating part 22 has an operating part body 32 provided with the erection operating lever 20, and a gripping part 34 continuously connected to the operating part body 32, and a proximal end part of the insertion part 24 is provided via a folding-preventing tube 38 on a distal end side of the gripping part 34. In addition, the gripping part 34 is a portion gripped by a surgeon in a case where the endoscope 10 is operated.

The operating part body 32 of the operating part 22 is provided with a universal cord 46. A light source connector 50 is provided on a distal end side of the universal cord 46. An electric connector 48 is provided so as to branch from the light source connector 50. Also, the electric connector 48 is connected to the processor device 14, and the light source connector 50 is connected to the light source device 16.

The insertion part 24 is configured such that the distal end part 26, a bending part 52, and a flexible part 54 are coupled to each other from a distal end side toward a proximal end side.

The following contents are provided inside the insertion part 24. That is, contents, such as a treatment tool channel 58 that guides a distal end part 56A of the treatment tool 56 of FIG. 1 to the distal end member 28 of FIG. 2, an erection operating wire 60 (hereinafter referred to as a wire 60) for performing the operation of changing the delivery direction of the distal end part 56A of the treatment tool 56 delivered from the distal end member 28, an erection operating wire channel 62 (hereinafter referred to as a wire channel 62) for guiding a distal end of the wire 60 to the distal end member 28, a light guide (not illustrated) that guides the illumination light, which is supplied from the light source device 16 of FIG. 1, to the distal end member 28 of FIG. 2, an air/water supply tube (not illustrated), an angle wire (not illustrated), and a signal cable (not illustrated) are provided. The wire channel 62 is an example of the wire insertion passage formed from the operating part 22 to the insertion part 24. The wire 60 is disposed to be inserted into the wire channel 62 so as to be movable forward and backward therethrough. Additionally, the distal end side of the wire 60 is attachably and detachably coupled to the elevator 30 as will be described below.

Referring back to FIG. 1, the operating part 22 is formed in a substantially cylindrical shape as a whole and has a longitudinal axis A in a Y(+)-Y(−) direction. Additionally, a pair of angle knobs 64 and 64, which bends the bending part 52, is disposed in the operating part 22. The pair of angle knobs 64 and 64 is provided on the same axis in a rotationally movable manner.

The bending part 52 has a structural body in which a plurality of angle rings (not illustrated) are coupled to each other in a rotationally movable manner. The bending part 52 is configured by covering an outer periphery of the structural body with a tubular net knit with metal wires and covering an outer peripheral surface of the net with a tubular outer cover made of rubber. For example, four angle wires (not illustrated) are disposed from the bending part 52 configured in this way to the angle knobs 64 and 64, and the bending part 52 is bent upward, downward, and rightward, and leftward by pushing and pulling of the angle wires by the rotational movement operation of the angle knobs 64 and 64.

An air/water supply button 66 and a suction button 68 are provided side by side by the operating part body 32 of the operating part 22. By operating the air/water supply button 66, air and water can be sprayed from an air/water supply nozzle 70 provided in the distal end member 28 of FIG. 2. Additionally, by operating the suction button 68 of FIG. 1, a body fluid, such as blood, can be suctioned from a suction port that also serves as a treatment tool delivery port 72 provided in the distal end member 28 of FIG. 2.

Moreover, the gripping part 34 of the operating part 22 of FIG. 1 is provided with a treatment tool introduction port 42 that introduces the treatment tool 56. The treatment tool 56, which is introduced with the distal end part 56A as a head from the treatment tool introduction port 42, is inserted through the treatment tool channel 58 of FIG. 2 inserted through the insertion part 24 and is delivered from the treatment tool delivery port 72 provided in the distal end member 28 to the outside.

Figure 9:
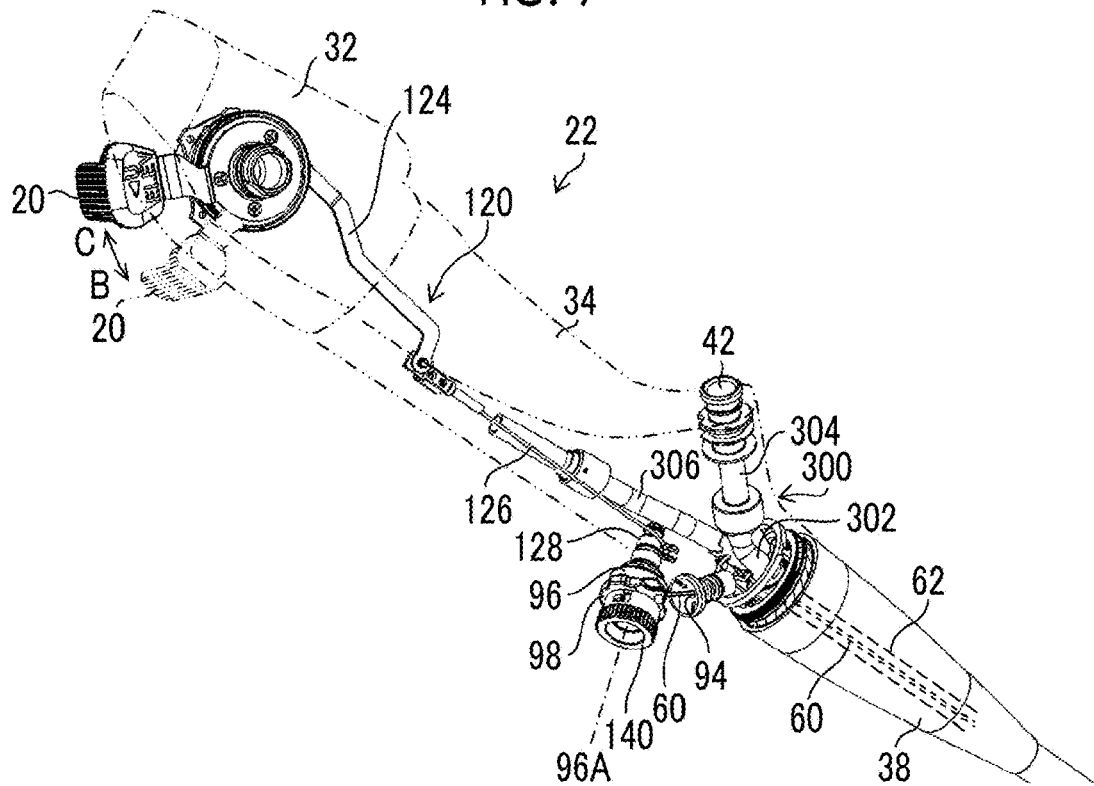
FIG. 9 is a perspective view illustrating the configuration of an erection operating mechanism.

Moreover, the erection operating lever 20 is rotatably provided in the operating part 22 of FIG. 1 coaxially with angle knobs 64 and 64. The erection operating lever 20 is rotationally operated by a surgeon's hand that grips the gripping part 34. In a case where the erection operating lever 20 is rotationally operated, the wire 60 of FIG. 2 is pushed and pulled by an erection operating mechanism 120 (refer to FIG. 9) and a rotating member 96 (refer to FIG. 9) that are operated in conjunction with the rotational operation of the erection operating lever 20. By this operation, the posture of the elevator 30 coupled to the distal end of the wire 60 is changed between the erected position of FIG. 3 and the lodged position of FIG. 2. In addition, the erection operating mechanism 120 and the rotating member 96 that are illustrated in FIG. 9 will be described below.

Referring back to FIG. 1, the flexible part 54 has a spiral tube (not illustrated) obtained by spirally winding a thin metallic beltlike sheet having elasticity. The flexible part 54 is configured by covering the outside of the spiral tube with a net knit with metal wires and covering an outer peripheral surface of the net with a tubular outer cover from a resin.

The endoscope 10 of the embodiment configured as described above is a side viewing endoscope used as a duodenoscope, and the insertion part 24 is inserted into the subject via an oral cavity. The insertion part 24 is inserted from the esophagus through the stomach to the duodenum, and treatment, such as a predetermined examination or curing, is performed.

In addition, in the embodiment, biopsy forceps having a cup capable of collecting a biological tissue at the distal end part 56A has been exemplified as the treatment tool 56, but the invention is not limited to this. For example, treatment tools, such as a contrast tube or a knife for endoscopic sphincterotomy (EST), are used as other treatment tools.

Next, the structure of the distal end part 26 of the insertion part 24 will be described.

As illustrated in FIG. 2, the distal end part 26 of the insertion part 24 is constituted of the distal end member 28, and a cap 76 that is attachably and detachably mounted to the distal end member 28. The cap 76 is formed to have a substantially tubular shape that is sealed on a distal end side thereof, and a substantially rectangular opening window 76A is formed in a portion of an outer peripheral surface of the cap 76. In a case where the cap 76 is mounted on the distal end member 28, the opening window 76A of the cap 76 communicates with the treatment tool delivery port 72 of the distal end member 28. As a result, the distal end part 56A of the treatment tool 56 delivered from the treatment tool delivery port 72 is delivered from the opening window 76A to the outside.

The cap 76 is made of a material with an elastic force, for example, a rubber material, such as fluororubber or silicone rubber, or a resin material, such as polysulfone. An engaging part (not illustrated) engaging with a groove (not illustrated) formed in the distal end member 28 is provided on a proximal end side of the cap 76, and the cap 76 is mounted on the distal end member 28 by engaging this engaging part with the groove of the distal end member 28. Additionally, in a case where the treatment of the endoscope 10 is completed, the cap 76 is detached from the distal end member 28 and cleaned and disinfected or is discarded as a disposable.

The distal end member 28 is made of a metallic material having corrosion resistance. Additionally, a partition wall 78 provided to protrude toward the distal end side and a partition wall 80 that faces the partition wall 78 are integrally provided in the distal end member 28. An elevator housing chamber 82 that houses the elevator 30 is formed between the partition wall 78 and the partition wall 80. The treatment tool delivery port 72 for delivering the treatment tool 56 to the outside is formed on a proximal end side of the elevator housing chamber 82, and a distal end part of the treatment tool channel 58 is connected to the treatment tool delivery port 72.

The treatment tool channel 58 is inserted through the insertion part 24 of FIG. 1. A proximal end part of the treatment tool channel 58 is connected to a distal end tube 302 of a branched tube 300 (refer to FIG. 9) provided inside the operating part 22.

The branched tube 300 has a well-known structure, a proximal end part thereof is branched to two pipe lines 304 and 306, and the treatment tool introduction port 42 is formed at a proximal end of one pipe line 304. Therefore, the distal end part 56A of the treatment tool 56 introduced from the treatment tool introduction port 42 is inserted through the treatment tool channel 58 via the pipe line 304 and is delivered from the treatment tool delivery port 72 of FIG. 2 to the elevator housing chamber 82. Then, the distal end part 56A of the treatment tool 56 delivered to the elevator housing chamber 82 is changed in delivery direction depending on the posture between the erected position and the lodged position of the elevator 30 disposed in the elevator housing chamber 82. Additionally, a distal end of a suction tube (not illustrated) that suctions a body fluid, such as blood, is connected to a proximal end of the other pipe line 306 of the branched tube 300 illustrated in FIG. 9.

Figure 4:
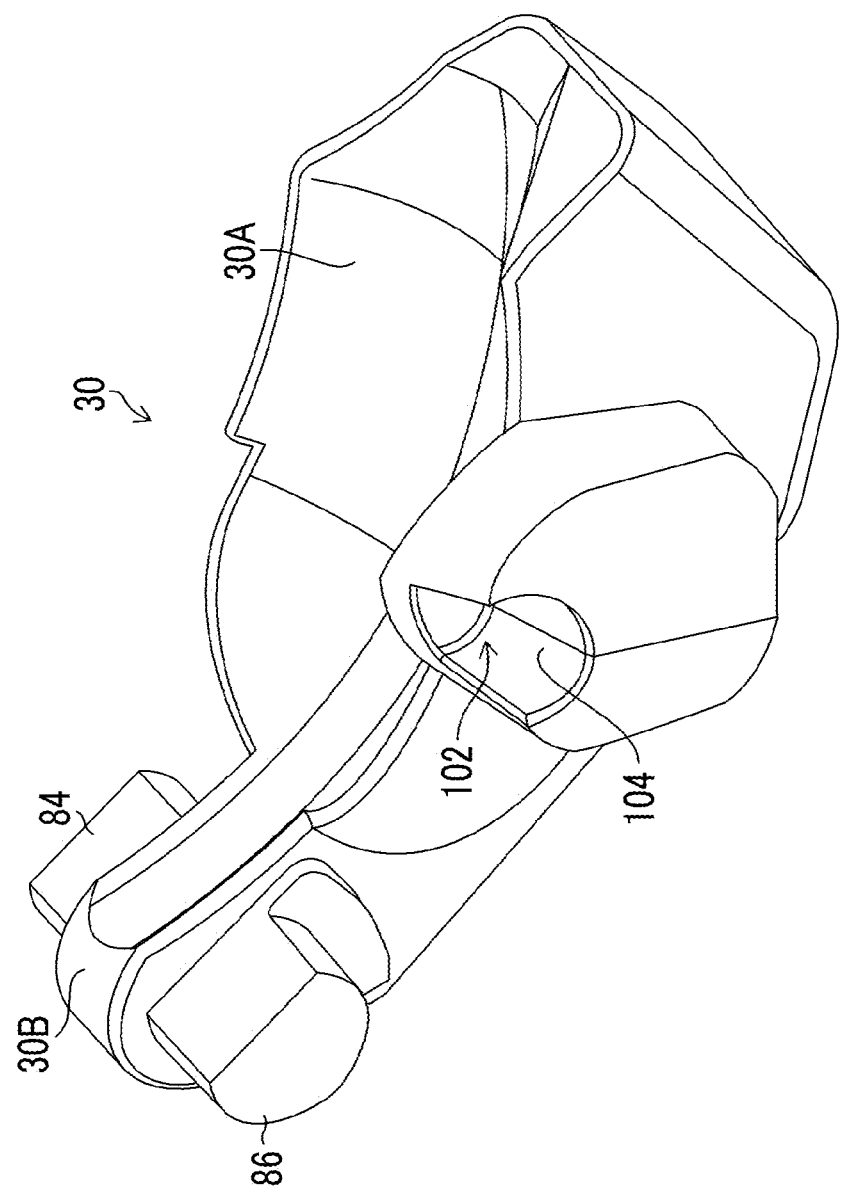
FIG. 4 is an enlarged perspective view of the elevator.

FIG. 4 is an enlarged perspective view of the elevator 30. As illustrated in FIG. 4, an upper surface of the elevator 30 is provided with a guide surface 30A. The distal end part 56A of the treatment tool 56 of FIG. 1 is delivered from the opening window 76A of the cap 76 of FIG. 2 to the outside along the guide surface 30A.

As illustrated in FIG. 4, both side surfaces of a proximal part 30B of the elevator 30 are provided with rotational movement shafts 84 and 86. An axial direction of the rotational movement shafts 84 and 86 is set as an X(+)-X(−) direction of FIG. 2 in a case where the elevator 30 is attached to the distal end member 28.

Figure 5:
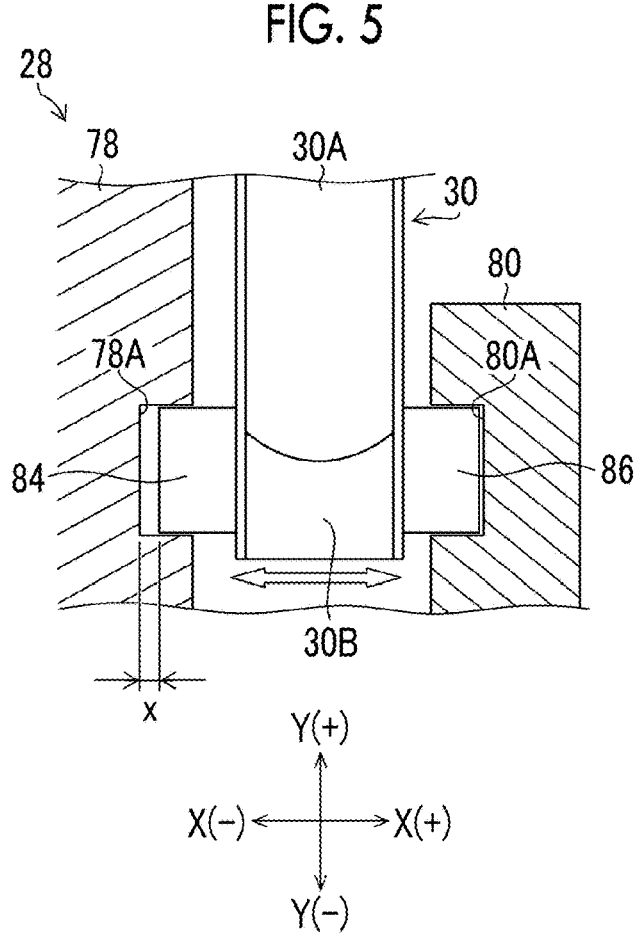
FIG. 5 is a cross-sectional view of main parts illustrating an attachment structure of the elevator with respect to the distal end member.

FIG. 5 is a cross-sectional view of main parts illustrating an attachment structure of the elevator 30 with respect to the distal end member 28. As illustrated in FIG. 5, the axes of the rotational movement shafts 84 and 86 are coaxially disposed via the proximal part 30B of the elevator 30, the rotational movement shaft 84 is fitted to a concave bearing part 78A of the partition wall 78 in a rotationally movable manner, and the rotational movement shaft 86 is fitted to a concave bearing part 80A of the partition wall 80 in a rotationally movable manner. Additionally, the rotational movement shafts 84 and 86 are mounted on the bearing parts 78A and 80A, respectively, with a predetermined rattling amount x in the axial direction of the rotational movement shafts 84 and 86. In a case where the rotational movement shafts 84 and 86 are biased to one side by utilizing the rattling amount x, a portion of one bearing part of the bearing parts 78A and 80A can be exposed and a brush can be easily inserted into the exposed portion. Thus, the cleaning performance of the bearing parts 78A and 80A is improved.

Meanwhile, as illustrated in FIGS. 2 and 3, an optical system housing chamber 88 is provided inside the partition wall 78. An illumination window 90 and an observation window 92 are disposed adjacent to each other at an upper part of the optical system housing chamber 88, and the air/water supply nozzle 70 directed to the observation window 92 is provided in the distal end member 28. The air/water supply nozzle 70 is connected to an air/water supply device (not illustrated) via the air/water supply tube (not illustrated) inserted through the insertion part 24, and air or water is sprayed from the air/water supply nozzle 70 toward the observation window 92 by operating the air/water supply button 66 of the operating part 22 illustrated in FIG. 1. As a result, the observation window 92 is cleaned.

An illumination unit (not illustrated) and an imaging unit (not illustrated) are housed inside the optical system housing chamber 88. The illumination unit comprises an illumination lens (not illustrated) installed inside the illumination window 90, and the light guide (not illustrated) disposed such that a distal end surface thereof faces the illumination lens. The light guide is disposed in the universal cord 46 via the operating part 22 from the insertion part 24 of the endoscope 10 and has a proximal end connected to the light source device 16 via the light source connector 50. As a result, the radiated light from the light source device 16 is transmitted via the light guide and is radiated from the illumination window 90 to the outside.

The aforementioned imaging unit comprises an imaging optical system (not illustrated) disposed inside the observation window 92, and a complementary metal oxide semiconductor (CMOS) type or charge coupled device (CCD) type image pickup element (not illustrated). The image pickup element is connected to the processor device 14 via the signal cable (not illustrated) inserted through the insertion part 24 of FIG. 1. After image pickup signals of a subject image obtained by the imaging unit is output to the processor device 14 via the signal cable and image-processed, the image pickup signals are displayed as the subject image on the display 18.

Figure 6:
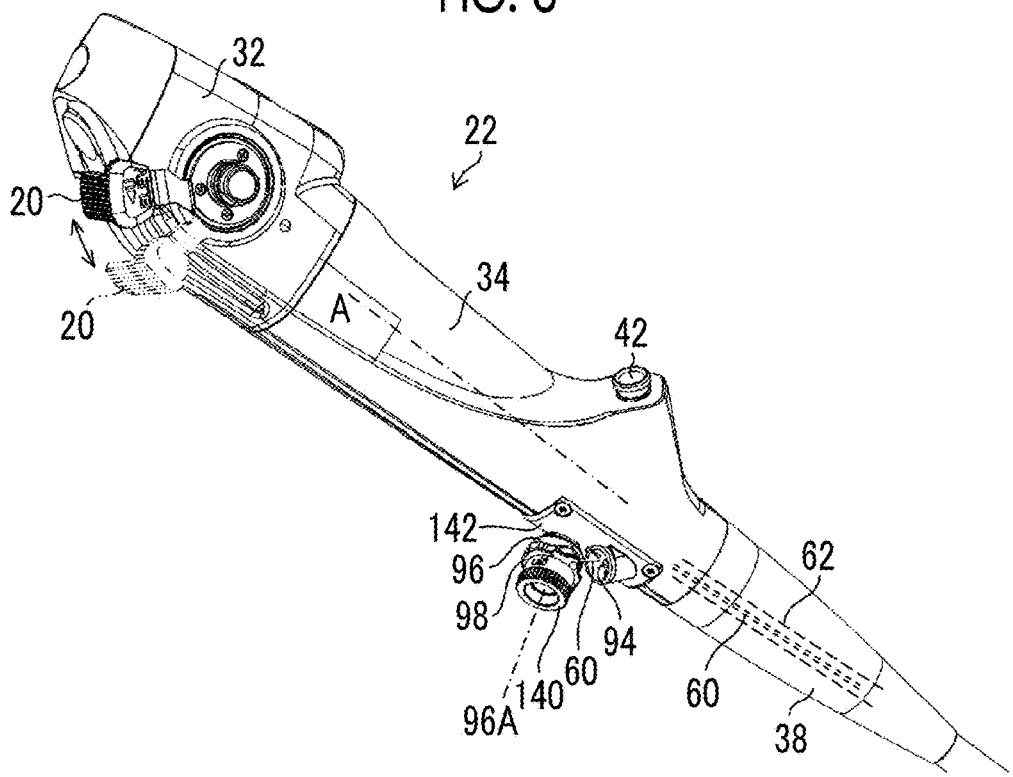
FIG. 6 is a perspective view illustrating the other side surface that faces one side surface of an operating part illustrated in FIG. 1.

Although overlapping the previous description, as for the wire 60 illustrated in FIGS. 2 and 3, the distal end of the wire 60 is disposed outside the delivery port 74 and is attachably and detachably coupled to the elevator 30. Additionally, as illustrated in FIG. 6, a proximal end side of the wire 60 is delivered from an opening part 94 disposed in the operating part 22 to the outside of the operating part 22 and is coupled to the rotating member 96. The opening part 94 is an opening part provided at a proximal end of the wire channel 62 illustrated in FIG. 2. Additionally, as illustrated in FIG. 6, the rotating member 96 is disposed to be exposed to the outside of the operating part 22 and is configured to be rotatable around a rotational axis 96A. The rotational axis 96A has a component in a direction obliquely inclined with respect to a direction orthogonal to the longitudinal axis of the operating part 22, that is, a direction orthogonal to a longitudinal direction along the longitudinal axis A of the operating part 22. By disposing the rotational axis 96A in an inclined manner in this way, the proximal end side of the wire 60 can be connected to the rotating member 96 without applying an excessive stress to the wire 60 disposed outside from the opening part 94. The rotating member 96 will be described below. In addition, FIG. 6 is a perspective view of the operating part 22 of FIG. 1 as viewed upward from below.

Next, an engaging structure in which the distal end of the wire 60 is attachably and detachably coupled to the elevator 30 will be described.

As illustrated in FIGS. 2 and 3, the distal end of the wire 60 is provided with an engaging member 100. Additionally, the elevator 30 is provided with a housing groove 102 that is attachably and detachably coupled to the engaging member 100 and is formed with an opening 104 on the X(+) direction side. As a result, the distal end of the wire 60 is coupled to the elevator 30 by housing the engaging member 100 provided at the distal end of the wire 60 in the housing groove 102 via the opening 104.

In the embodiment, the engaging member 100 is a spherical body, and the housing groove 102 is a spherical recess that houses the spherical engaging member 100. In addition, although the shapes of the engaging member 100 and the housing groove 102 are not limited to the above shapes, the sliding resistance between the engaging member 100 and the housing groove 102 that occurs due to the push/pull operation of the wire 60 can be reduced by forming the engaging member 100 as a spherical body and forming the housing groove 102 as a spherical recess. Therefore, the push/pull operation of the wire 60 can be smoothly performed.

Additionally, the distal end member 28 is provided with an engagement guide part 106 provided continuously with the housing groove 102 at the erected position of FIG. 3. The engagement guide part 106 has the function of guiding the engaging member 100, which is delivered from the delivery port 74, to the opening 104 of the housing groove 102. The delivery port 74 is provided in the distal end member 28 and communicates with the opening part 94 (refer to FIG. 6) of the proximal end of the wire channel 62 via the wire channel 62.

According to the endoscope 10 having such an engagement guide part 106, in a case where the wire 60 is introduced with the engaging member 100 as a head from the opening part 94 of the wire channel 62, the engaging member 100 is inserted through the wire channel 62 (refer to FIG. 2) and is delivered from the delivery port 74 to the outside. Then, the engaging member 100 is guided toward the opening 104 of the housing groove 102 of the elevator 30 by the engagement guide part 106 by continuing the introduction operation of the wire 60 and is engaged with the housing groove 102 from the opening 104. As a result, according to the endoscope 10 of the embodiment, the engaging member 100 of the wire 60 can be engaged with the housing groove 102 of the elevator 30 simply by the introduction operation of the wire 60.

Figure 7:
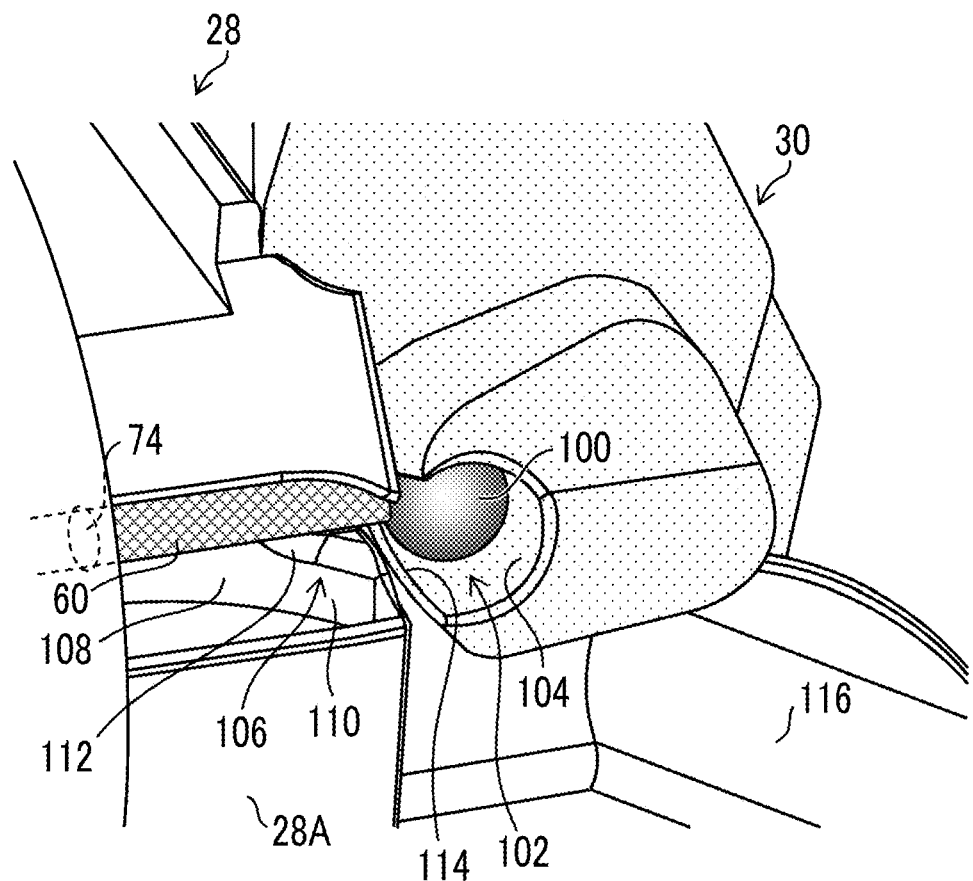
FIG. 7 is an enlarged perspective view in which an engaging part is housed in a housing part via an engagement guide part.
Figure 8:
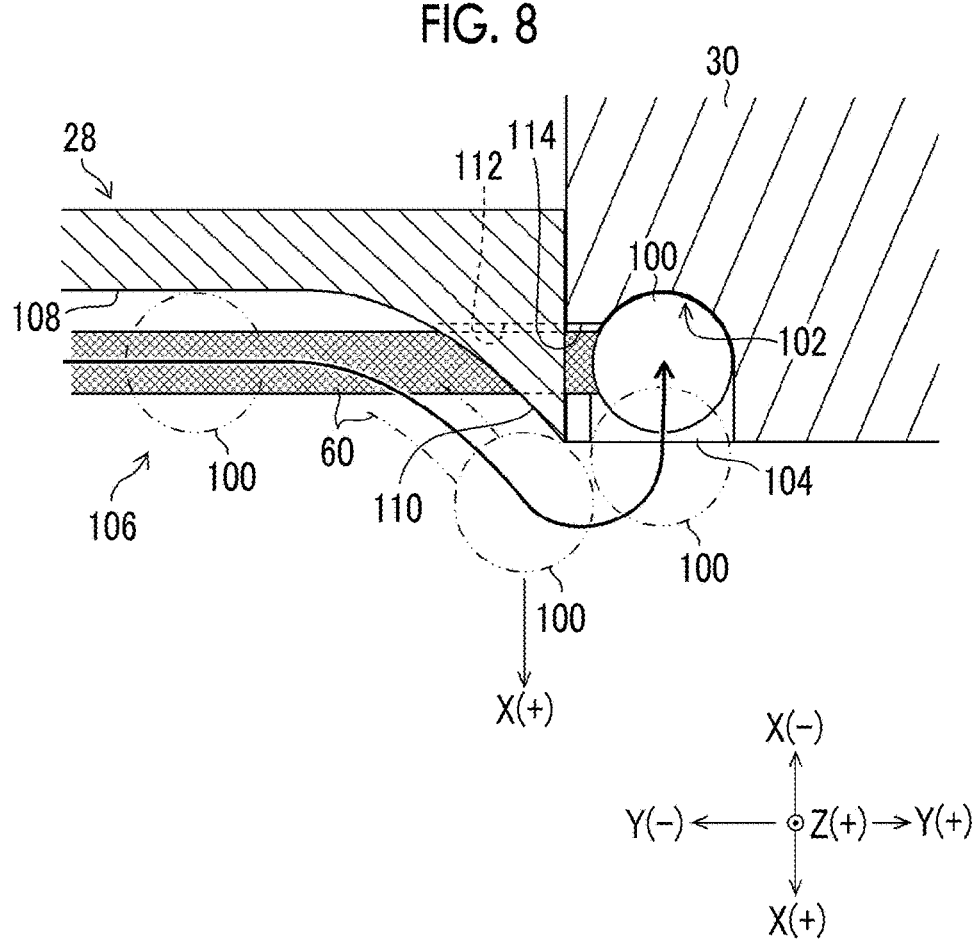
FIG. 8 is an explanatory view of the operation in which the engaging part is guided by the engagement guide part and is housed in the housing part.

FIG. 7 is an enlarged perspective view in which the engaging member 100 is engaged with the housing groove 102 via the engagement guide part 106. FIG. 8 is an explanatory view sequentially illustrating the operation until the engaging member 100 is guided to the engagement guide part 106 and engaged with the housing groove 102.

As illustrated in FIGS. 7 and 8, the engagement guide part 106 comprises an engagement guide path 108 that guides the engaging member 100, which is delivered from the delivery port 74, to the opening 104 of the housing groove 102, and a deformation generating part 110 provided continuously with the opening 104 of the housing groove 102 within the engagement guide path 108. The deformation generating part 110 comes into contact with the engaging member 100 that advances in the Y(+) direction toward the opening 104 within the engagement guide path 108 and guides the engaging member 100 in the X(+) direction while guiding the engaging member 100 in the Y(+) direction.

As a result, the distal end of the wire 60 is elastically deformed in a direction (X(+) direction) gradually away from the opening 104 as the engaging member 100 approaches the opening 104 along the engagement guide path 108. In a case where the engaging member 100 that advances within the engagement guide path 108 has passed through the deformation generating part 110, the engaging member 100 is moved in the X(−) direction by a restoring force of the wire 60 and is engaged with the housing groove 102 from the opening 104.

The engagement guide path 108 is formed by concavely cutting away a portion of a peripheral surface 28A of the distal end member 28 and is a surface that is gradually inclined in the X(+) direction from the delivery port 74 toward the Y(+) direction. The deformation generating part 110 is formed on a distal end side of the engagement guide path 108.

Additionally, a groove 112 for allowing the distal end of the wire 60 to sink and escape in a case where the engaging member 100 is engaged with the housing groove 102 is formed in the engagement guide part 106. Additionally, a groove 114 for allowing the distal end of the wire 60 to sink and escape in a case where the engaging member 100 is engaged with the housing groove 102 is also formed on a proximal end side of the housing groove 102 of the elevator 30. The width dimension of the groove 112 in a direction orthogonal to the paper plane of FIG. 8 is larger than the diameter of the wire 60 and is smaller than the diameter of the engaging member 100 such that the engaging member 100 passing through the deformation generating part 110 does not sink in the groove 112. Additionally, the width dimension of the groove 114 of in the direction orthogonal to the paper plane of FIG. 8 is larger than the diameter of the wire 60 and is smaller than the diameter of the engaging member 100 such that the engaging member 100 engaged with the housing groove 102 does not slip out in the Y(−) direction.

Additionally, the engagement guide part 106 has a form that is suitable in a case where the engaging member 100 is engaged with the housing groove 102 in a state where the elevator 30 is located at the erected position. That is, as illustrated in FIG. 7, the housing groove 102 is disposed at a position that faces the delivery port 74 in a state where the elevator 30 is located at the erected position. Therefore, by advancing the engaging member 100 straight from the delivery port 74, the engaging member 100 can be engaged with the housing groove 102 of the elevator 30 located at the erected position via the engagement guide part 106.

Next, a separation structure for separating the engaging member 100 of the wire 60 engaged with the housing groove 102 of the elevator 30 from the housing groove 102 will be described.

As illustrated in FIGS. 2 and 3, the distal end member 28 is provided with a separation guide surface 116, and the separation guide surface 116 is provided on an upper surface of the partition wall 80. The separation guide surface 116 is a guide surface that is inclined in the Z(−) direction toward the X(+) direction. Additionally, the separation guide surface 116 functions as a surface of guiding the wire 60 in a direction in which the engaging member 100 is separated from the inside of the housing groove 102 to the outside of the opening 104 in a case where the wire 60 is further pushed in a state where the engaging member 100 is engaged with the housing groove 102 and the elevator 30 is located at the lodged position.

According to the separation structure configured in this way, the elevator 30 is located at the lodged position of FIG. 2 from the erected position of FIG. 3 by detaching the proximal end side of the wire 60 from the rotating member 96 of FIG. 6, and thereafter operating to push the wire 60 from the opening part 94 of the wire channel 62. Thereafter, in a case where the wire 60 is further pushed, the wire 60 is guided in the X(+) direction in which the engaging member 100 is separated from the inside of the housing groove 102 to the outside the opening 104 by the separation guide surface 116 of the distal end member 28. As a result, the engaging member 100 is easily separated from the inside of the housing groove 102 to the outside of the opening 104 by the restoring force of the wire 60.

Next, the erection operating mechanism 120 illustrated in FIG. 9 will be described.

FIG. 9 is a perspective view illustrating the configuration of the erection operating mechanism 120. In addition, in FIG. 9, a sheathing case (not illustrated) of the operating part 22 is omitted, and the inside of the operating part 22 is illustrated in a simplified manner.

In the erection operating mechanism 120 illustrated in FIG. 9, constituent elements of the respective parts that constitute the erection operating mechanism 120 are configured to be continuously provided from the operating part body 32 to the gripping part 34 inside the operating part 22.

The erection operating mechanism 120 is a power transmission mechanism that couples the erection operating lever 20 and the rotating member 96 to each other and transmits the rotational operation of the erection operating lever 20 to the rotating member 96.

The erection operating mechanism 120 comprises an arm 124 that converts the rotary motion of the erection operating lever 20 into a linear motion, a wire 126 that is coupled to the arm 124 and is pushed and pulled by the arm 124, and a rotational driving unit 128 (refer to FIG. 10) that is coupled to the wire 126. The rotating member 96 is attached to the rotational driving unit 128.

Figure 10:
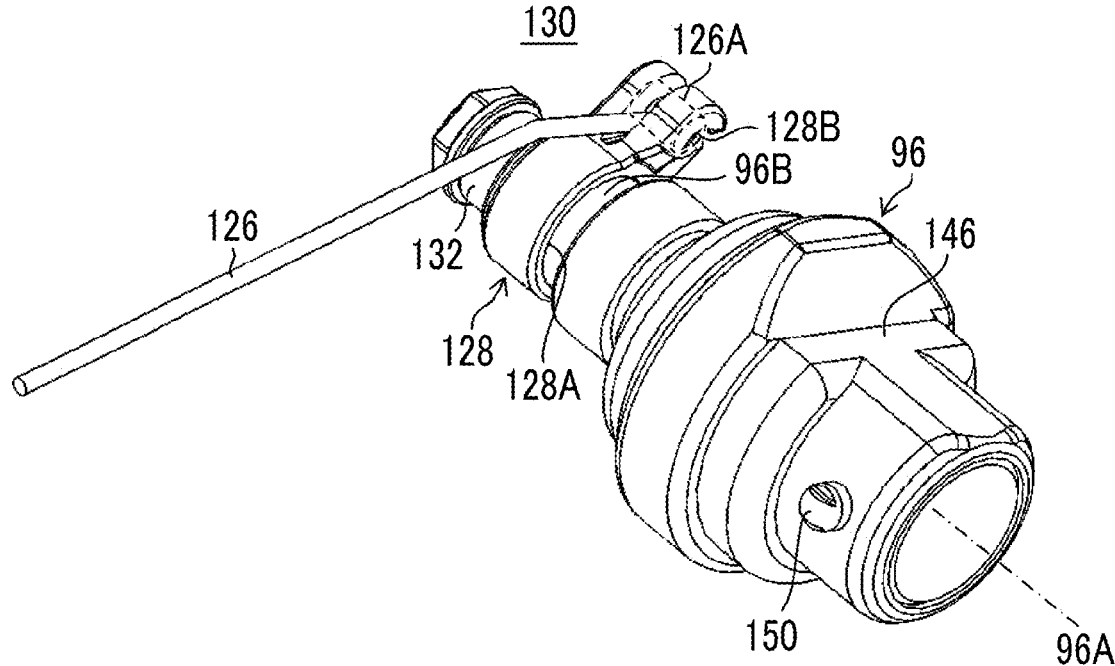
FIG. 10 is an enlarged perspective view of main parts of a rotational driving unit in a case where a rotating member is located at a lodged position.

FIG. 10 is an enlarged perspective view of main parts illustrating a coupling structure between the wire 126 and the rotational driving unit 128.

As illustrated in FIG. 10, the rotational driving unit 128 is disposed in a housing space 130 formed inside the operating part 22. Additionally, the rotational driving unit 128 is supported so as to be rotatable around the rotational axis 96A of the rotating member 96 with respect to a bearing part 132 disposed in the housing space 130. Additionally, the rotational driving unit 128 comprises a circular opening part 128A centered on the rotational axis 96A, and a proximal part 96B of the rotating member 96 is fitted to the opening part 128A. Additionally, the rotational driving unit 128 comprises a cylindrical wire engaged part 128B at a position offset from the rotational axis 96A. The wire 126 comprises a columnar wire engaging part 126A at the distal end thereof. The wire 126 and the rotational driving unit 128 are coupled to each other by engaging the wire engaging part 126A with the wire engaged part 128B. Then, as the wire 126 is pushed and pulled by the rotational operation of the erection operating lever 20 (refer to FIG. 9), the rotational driving unit 128 is rotated around the rotational axis 96A. As a result, the rotating member 96 is rotated around the rotational axis 96A.

Next, the operation of the erection operating mechanism 120 illustrated in FIG. 9 will be described.

In a case where the erection operating lever 20 is rotationally operated in a direction of arrow B from a position illustrated by a solid line to a position illustrated by a two-dot chain line, the arm 124 performs a linear motion toward a proximal end side of the operating part 22 along the longitudinal axis A of the operating part 22. Then, the wire 126 is pulled to the proximal end side in conjunction with the operation of the arm 124.

Here, FIG. 10 is an explanatory view illustrating the position of the rotational driving unit 128 in a case where the erection operating lever 20 is located at the position illustrated by the solid line of FIG. 9, i.e., the elevator 30 is located at the lodged position (refer to FIG. 2). Additionally, the erection operating lever 20 is located at the position illustrated by the two-dot chain line of FIG. 9, i.e., the elevator 30 is located at the erected position (refer to FIG. 3).

Figure 11:
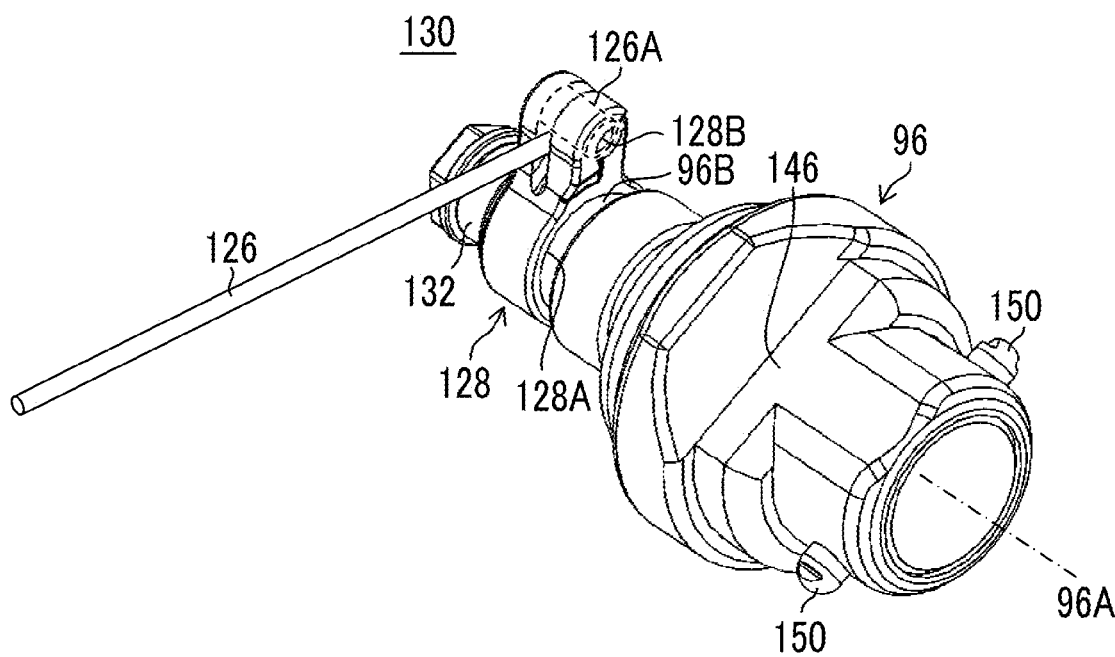
FIG. 11 is an enlarged perspective view of the main parts of the rotational driving unit in a case where the rotating member is located at an erected position.

Referring back to FIG. 9, in a case where the rotational driving unit 128 performs a rotary motion from the position of FIG. 10 toward the position of FIG. 11 by the operation in the direction of arrow B of the erection operating lever 20, the rotating member 96 rotates in the counterclockwise direction around the rotational axis 96A together with the rotational driving unit 128. The proximal end side of the wire 60 is coupled to the rotating member 96 as will be described below. Hence, in a case where the rotating member 96 rotates from the position of FIG. 10 toward the position of FIG. 11, the wire 60 is pulled, and the elevator 30 moves to the erected position of FIG. 3.

On the other hand, contrary to this operation, in a case where the erection operating lever 20 is rotationally operated in a direction of arrow C from the position illustrated by the two-dot chain line of FIG. 9 to the position illustrated by the solid line, the arm 124 performs a linear motion toward the distal end side of the operating part 22 along the longitudinal axis A of the operating part 22. Then, the wire 126 is pushed to the distal end side in conjunction with the operation of the arm 124.

As a result, since the rotational driving unit 128 performs a rotary motion from the position of FIG. 11 toward the position of FIG. 10, the rotating member 96 rotates clockwise around the rotational axis 96A together with the rotational driving unit 128. The wire 60 is pushed by the rotation of the rotating member 96, and the elevator 30 moves to the lodged position of FIG. 2.

The above operation is the operation of the erection operating mechanism 120.

Next, a connection structure of a first embodiment in which the proximal end side of the wire 60 is connected to the rotating member 96 will be described with reference to FIGS. 12, 13, and 14.

Figure 12:
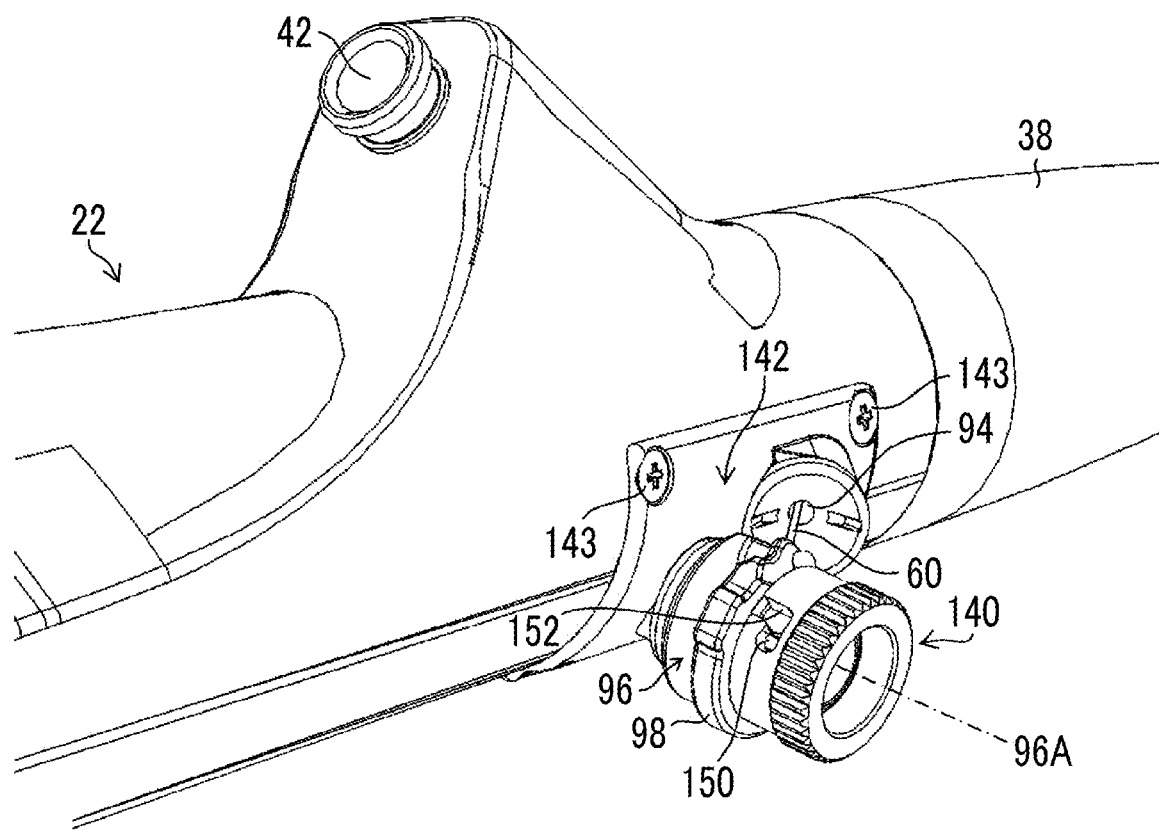
FIG. 12 is a perspective view illustrating a connection structure of a first embodiment.

FIG. 12 is a perspective view illustrating the connection structure of the first embodiment in which the proximal end side of the wire 60 is connected to the rotating member 96. In FIG. 12, the rotating member 96, the engaging part 98 provided on the proximal end side of the wire 60, and the locking member 140 are illustrated, and a state where the engaging part 98 and the locking member 140 are mounted on the rotating member 96 is illustrated.

Figure 13:
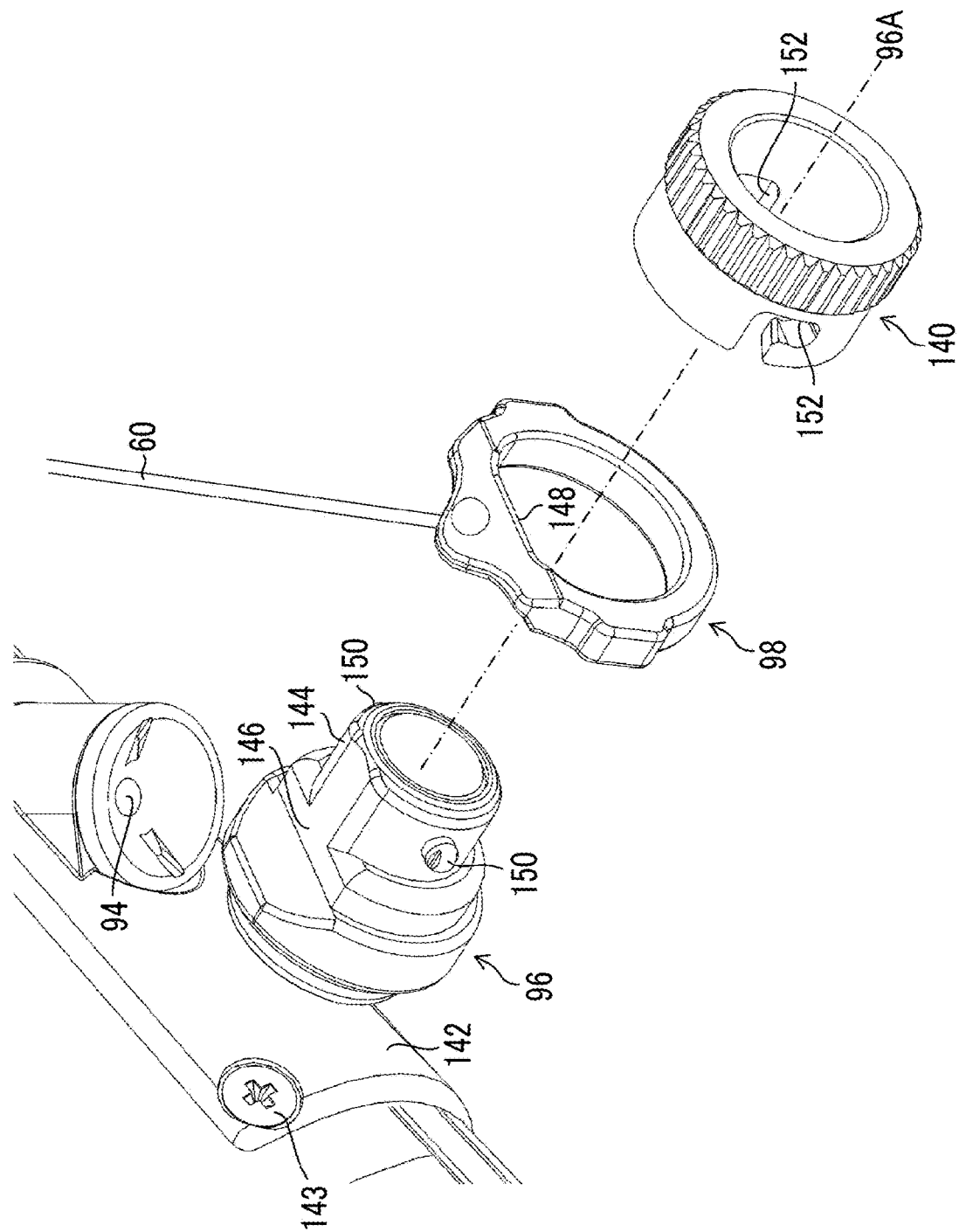
FIG. 13 is an assembling perspective view of the connection structure illustrated in FIG. 12.

Additionally, FIG. 13 is an assembling perspective view of the connection structure illustrated in FIG. 12. FIG. 14 is an explanatory view in which the engaging part 98 is engaged with the rotating member 96.

As illustrated in FIG. 12, the rotating member 96 is disposed to be exposed to the outside of the operating part 22 via a cover 142 attached to the operating part 22. The cover 142 blocks an opening part (not illustrated) formed in the operating part 22, and the cover 142 is fixed to the operating part 22 via a packing (not illustrated). As a result, the housing space 130 illustrated in FIG. 10 is sealed. In addition, the cover 142 is fixed to the operating part 22 by a plurality of screws 143.

The rotating member 96 illustrated in FIG. 12 protrudes from the opening part (not illustrated) formed in the cover 142 to the outside and is rotatably mounted on the opening part via an O-ring (not illustrated).

As illustrated in FIG. 13, the rotating member 96 is provided with an engaged part 144 that is formed substantially in a shaft shape. Additionally, the engaging part 98 mounted on the rotating member 96 is formed substantially in a ring shape so as to be engaged with the engaged part 144.

The engaged part 144 has a rotation restricting part 146 that restricts relative rotation of the engaging part 98 engaging with the engaged part 144. The rotation restricting part 146 is constituted as a D-cut rotation restricting surface as an example. Additionally, the engaging part 98 has a rotation restricting part 148 engaging with the rotation restricting part 146. This rotation restricting part 148, similarly to the rotation restricting part 146, is constituted as a D-cut rotation restricting surface.

Figure 14:
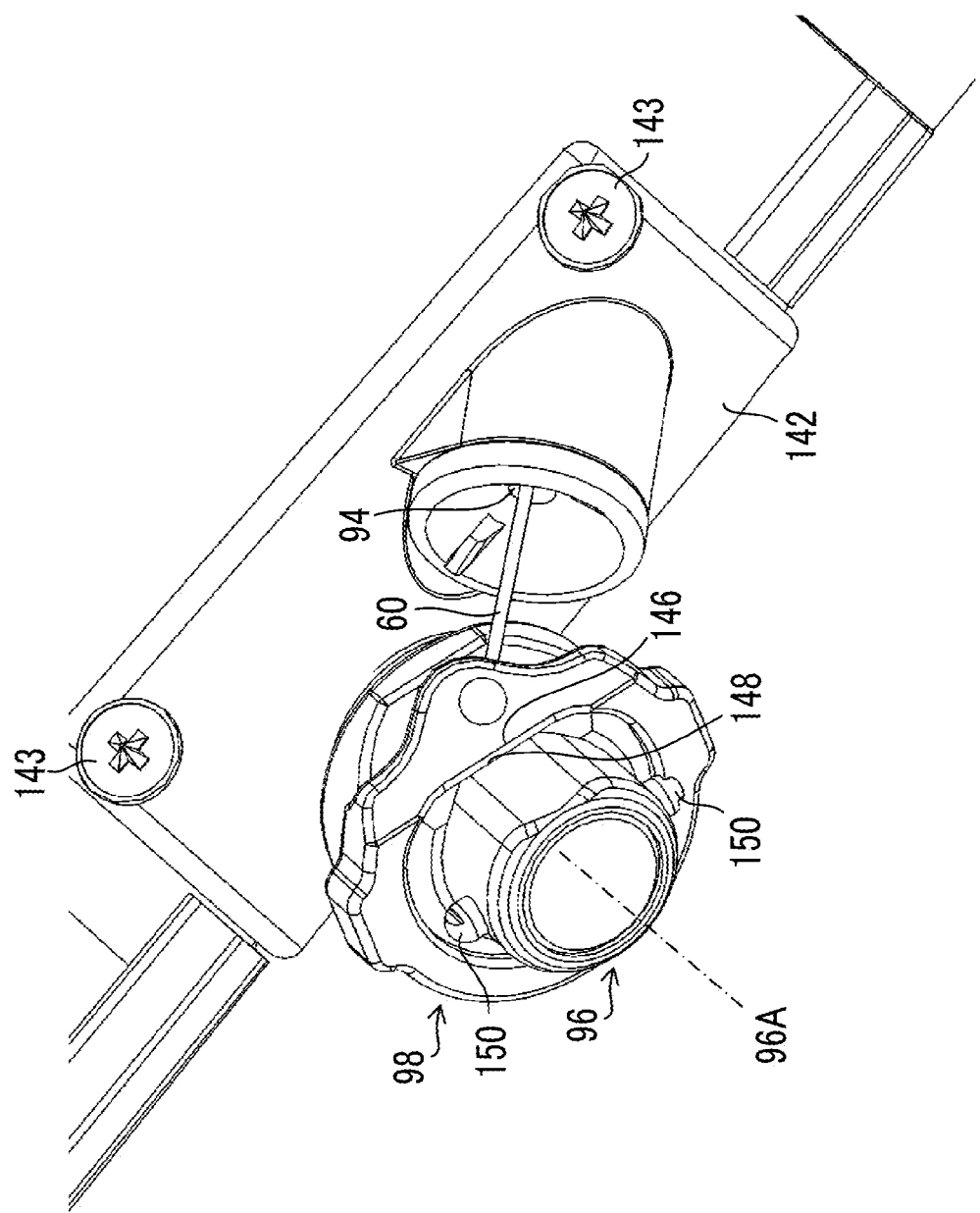
FIG. 14 is an explanatory view in which the engaging part is engageably and disengageably engaged with the rotating member.

In a case where the engaging part 98 engages with the engaged part 144 such that the rotation restricting part 148 is engaged with the rotation restricting part 146, as illustrated in FIG. 14, the engaging part 98 is engageably and disengageably engaged with the engaged part 144, and the relative rotation of the engaging part 98 with respect to the engaged part 144 is restricted. Since the connection structure of the first embodiment comprises such rotation restricting parts 146 and 148, the engaging part 98 can be reliably rotated together with the rotating member 96.

Figure 15:
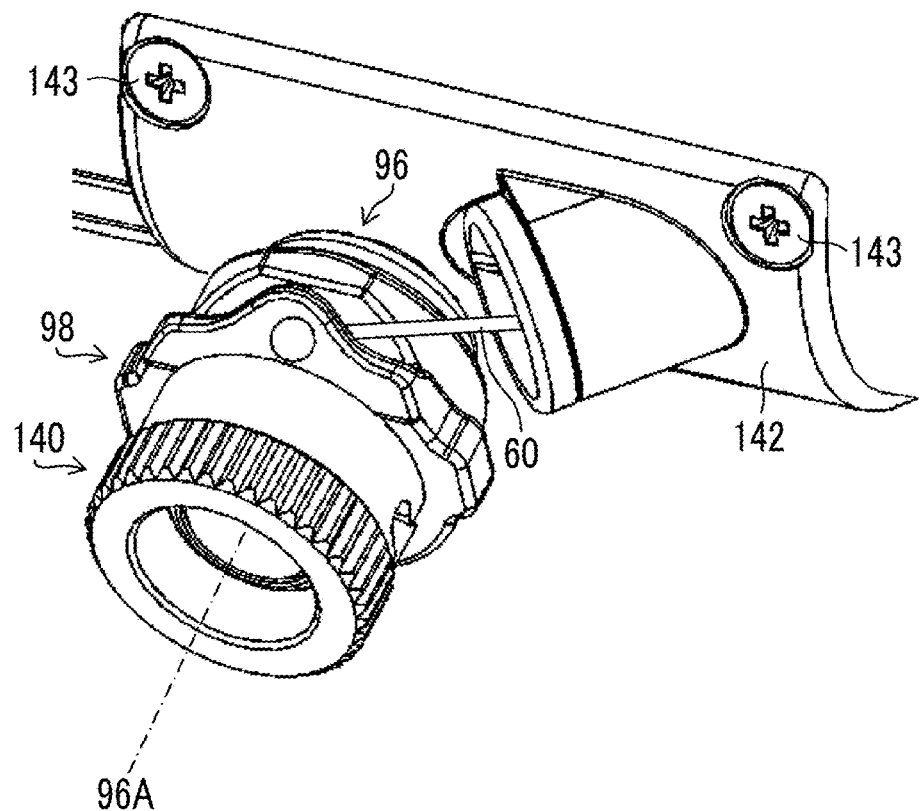
FIG. 15 is an explanatory view of the connection structure illustrating an operation in a case where the wire is pulled.
Figure 16:
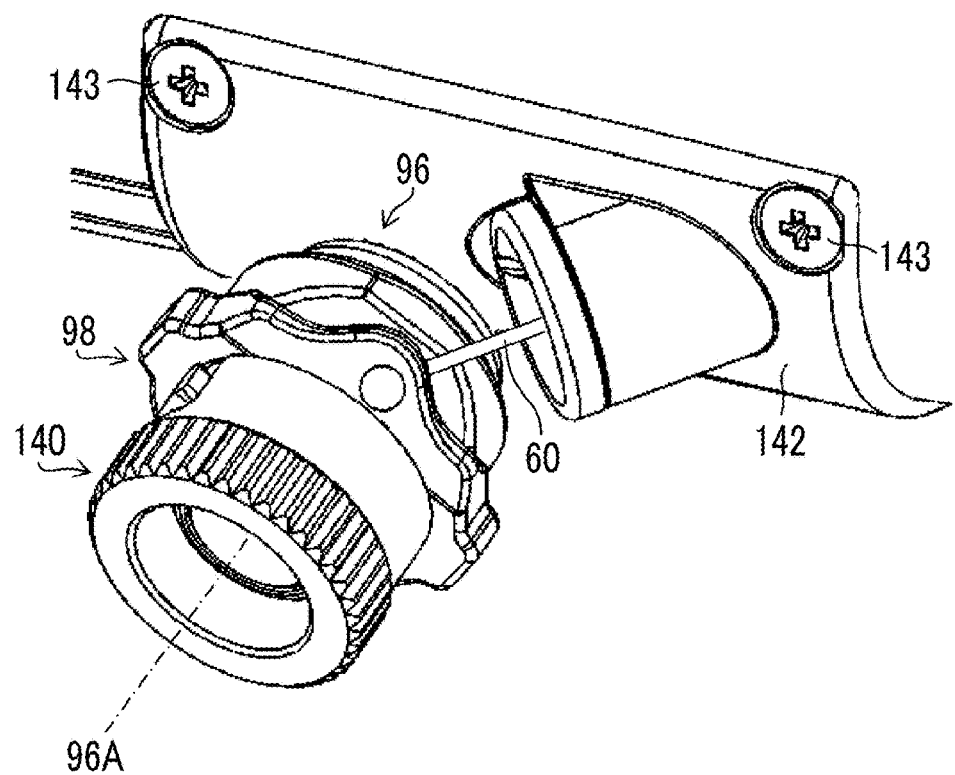
FIG. 16 is an explanatory view of the connection structure illustrating an operation in a case where the wire is pushed.

Hence, according to the connection structure of the first embodiment, in a case where the rotating member 96 is rotated from the position of FIG. 10 toward the position of FIG. 11 by the operation of the erection operating lever 20 (refer to FIG. 9) as illustrated in FIG. 15, the wire 60 is pulled by the rotating member 96 via the engaging part 98. Additionally, in a case where the rotating member 96 is rotated from the position of FIG. 11 toward the position of FIG. 10 by the operation of the erection operating lever 20, as illustrated in FIG. 16, the wire 60 is pushed by the rotating member 96 via the engaging part 98. In addition, in the connection structure of the first embodiment, the D-cut rotation restricting part 146 is exemplified as the rotation restricting part. However, the invention is not limited to this, for example, a dovetail groove-like rotation restricting part may be provided.

Figure 17:
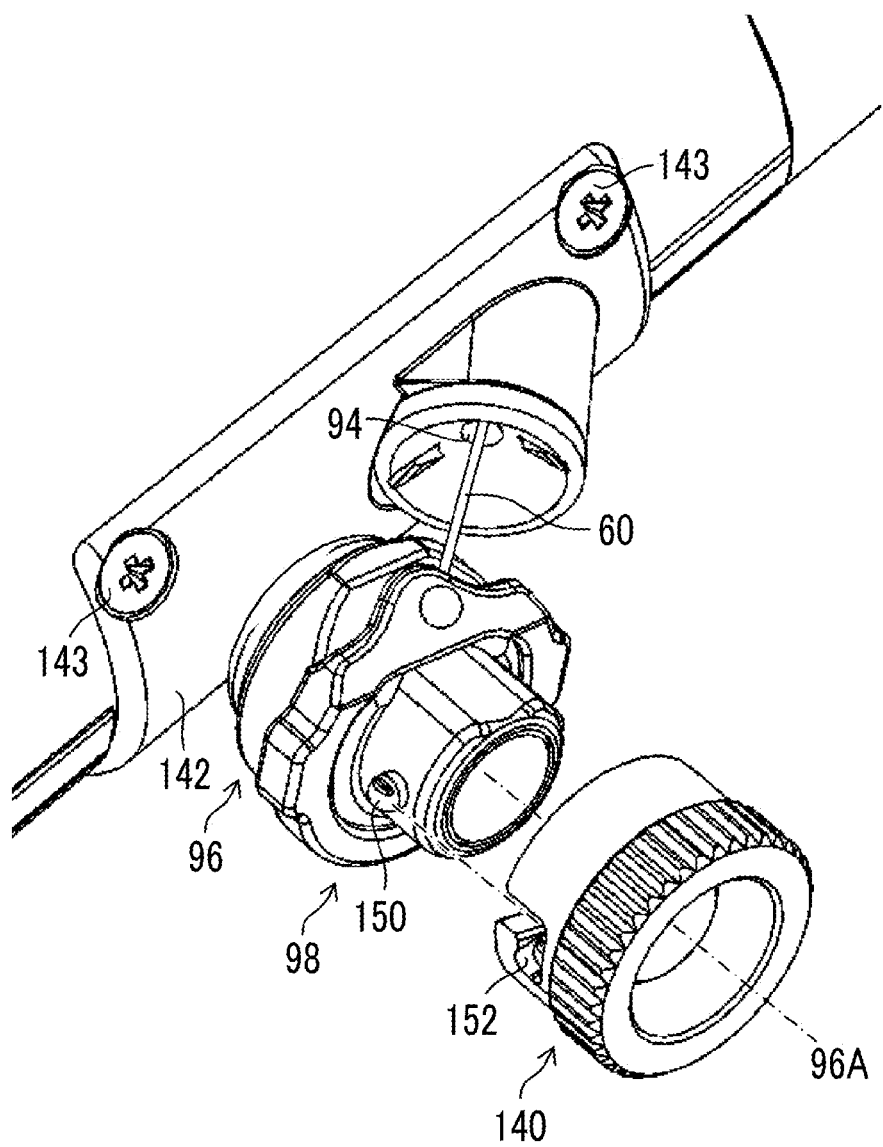
FIG. 17 is an explanatory view of an unlocked position of the connection structure of the first embodiment.

Meanwhile, as illustrated in FIG. 13, the locking member 140 is formed in a cylindrical shape and is attachably and detachably mounted on the rotating member 96. The locking member 140 is configured to be switchable between a locked position and an unlocked position by being rotated around the rotational axis 96A. That is, the locking member 140 is switched between a locked position where release of an engaged state between the engaged part 144 (refer to FIG. 13) and the engaging part 98 is prevented as illustrated in FIG. 12 and an unlocked position where the release of the engaged state between the engaged part 144 and the engaging part 98 is allowed as illustrated in FIG. 17. In addition, FIG. 17 illustrates that the locking member 140 is separated from the rotating member 96 in order to describe the unlocked position easily. Hereinafter, a configuration that enables the switching of the locking member 140 will be described.

As illustrated in FIG. 13, the rotating member 96 has a pair of engaging projections 150 on an outer peripheral surface of the rotating member 96, and the locking member 140 has L-shaped engaging grooves 152 with which the engaging projections 150 attachably and detachably engages. The locking member 140 is switched between a locked position where the engaging projections 150 and the engaging grooves 152 engage with each other(refer to FIG. 12) and an unlocked position where the engagement between the engaging projections 150 and the engaging grooves 152 are released (refer to FIG. 17) by being rotated in a state where the locking member is mounted on the rotating member 96. That is, by comprising the engaging projections 150 and the engaging grooves 152, the locking member 140 is switchable between the locked position and the unlocked position. In addition, the locked position illustrated in FIG. 12 is a position where slip-out of the engaging part 98 from the rotating member 96 is prevented, and the unlocked position illustrated in FIG. 17 is a position where the locking member 140 can be detached from the rotating member 96.

Next, the connection work of connecting the proximal end side of the wire 60 to the rotating member 96 by the connection structure of the first embodiment will be described.

Before the proximal end side of the wire 60 is connected to the rotating member 96, the coupling work of coupling the distal end of the wire 60 to the elevator 30 is performed. In this coupling work, first, the wire 60 is introduced with the engaging member 100 as a head from the opening part 94 of FIG. 13 in a state (refer to FIG. 3) where the elevator 30 is located at the erected position. As a result, the engaging member 100 is delivered from the delivery port 74 to the outside via the wire channel 62 (refer to FIG. 3). Then, the engaging member 100 is guided toward the opening 104 of the housing groove 102 of the elevator 30 by the engagement guide part 106 of FIG. 3 by continuing the introduction operation of the wire 60 and is engaged with the housing groove 102 from the opening 104. Thus, the coupling work of coupling the distal end of the wire 60 to the elevator 30 is completed.

Next, the connection work of connecting the proximal end side of the wire 60 to the rotating member 96 is performed. In this connection work, as illustrated in FIG. 14, the engaging part 98 is engaged with the engaged part 144 such that the rotation restricting part 148 of the engaging part 98 engages with the rotation restricting part 146 of the rotating member 96. The proximal end side of the wire 60 can be connected to the rotating member 96 by this work.

Hence, according to the connection structure of the first embodiment, the proximal end side of the wire 60 can be easily connected to the rotating member 96. Additionally, in a case where the locking member 140 is mounted on the rotating member 96 and located at the locked position, the slip-out of the engaging part 98 from the rotating member 96 can be prevented.

After connection work is performed in this way, the endoscope 10 is brought into a usable state. As a result, various kinds of examination or treatment are performed using the endoscope 10.

Next, in a case where the endoscope 10 is cleaned after various kinds of examination or treatment are performed using the endoscope 10, the following work is carried out.

First, the cap 76 illustrated in FIG. 2 is detached from the distal end member 28. Next, the proximal end side of the wire 60 is detached from the rotating member 96 of FIG. 14.

In this detachment work, first, the connection structure of the first embodiment switches the locking member 140 to the unlocked position (refer to FIG. 17) and detaches the locking member 140 from the rotating member 96. Next, the engaging part 98 is pulled out from the engaged part 144. The detachment work is completed by this work. Therefore, according to the connection structure of the first embodiment, the proximal end side of the wire 60 can be easily detached from the rotating member 96.

Next, in a case where the elevator 30 is located at the erected position of FIG. 3, the wire 60 is pushed from the opening part 94 illustrated in FIG. 13, and the elevator 30 is located at the lodged position of FIG. 2 from the erected position of FIG. 3. In addition, in a case where the elevator 30 is located in advance at the lodged position of FIG. 2, the above operation becomes unnecessary. Thereafter, the wire 60 is further pushed so as to separate the engaging member 100 from the inside of the housing groove 102 to the outside of the opening 104. By this work, the distal end of the wire 60 is detached from the elevator 30. Next, the wire 60 is pulled out from the opening part 94 to the outside to empty the wire channel 62. Thereafter, the distal end member 28, the elevator 30, and the wire channel 62 are cleaned.

According to the connection structure of the first embodiment, the rotating member 96 to which the proximal end side of the wire 60 is connected is disposed to be exposed to the outside of the operating part 22. Since the rotating member 96 push and pulls the wire 60 by the rotation of the rotating member 96, the space required for the push/pull operation of the wire 60 can be made smaller compared to a form in which a connection tool is slidingly moved the outside of an operating part. Therefore, the operability of the operating part 22 is maintained.

Hence, according to the connection structure of the first embodiment, the attachment and detachment work of the proximal end side of the wire 60 can be easily performed without impairing the operability of the operating part. In addition, since the rotating member 96 is provided even in the connection structure of the respective embodiments to be described below, the operability of the operating part 22 is maintained similarly.

Additionally, in the connection structure of the first embodiment, a form in which the locking member 140 is used has been illustrated as a more preferable form. However, the locking member 140 may not be necessarily used as long as the engaged state between the engaged part 144 and the engaging part 98 can be maintained.

Next, a connection structure of a second embodiment in which the proximal end side of the wire 60 is connected to the rotating member 96 will be described with reference to FIGS. 18 to 21.

In addition, in describing the connection structure of the second embodiment, the same or similar members as those of the connection structure of the first embodiment described in FIGS. 9 to 17 will be designated by the same reference signs and described.

Figure 18:
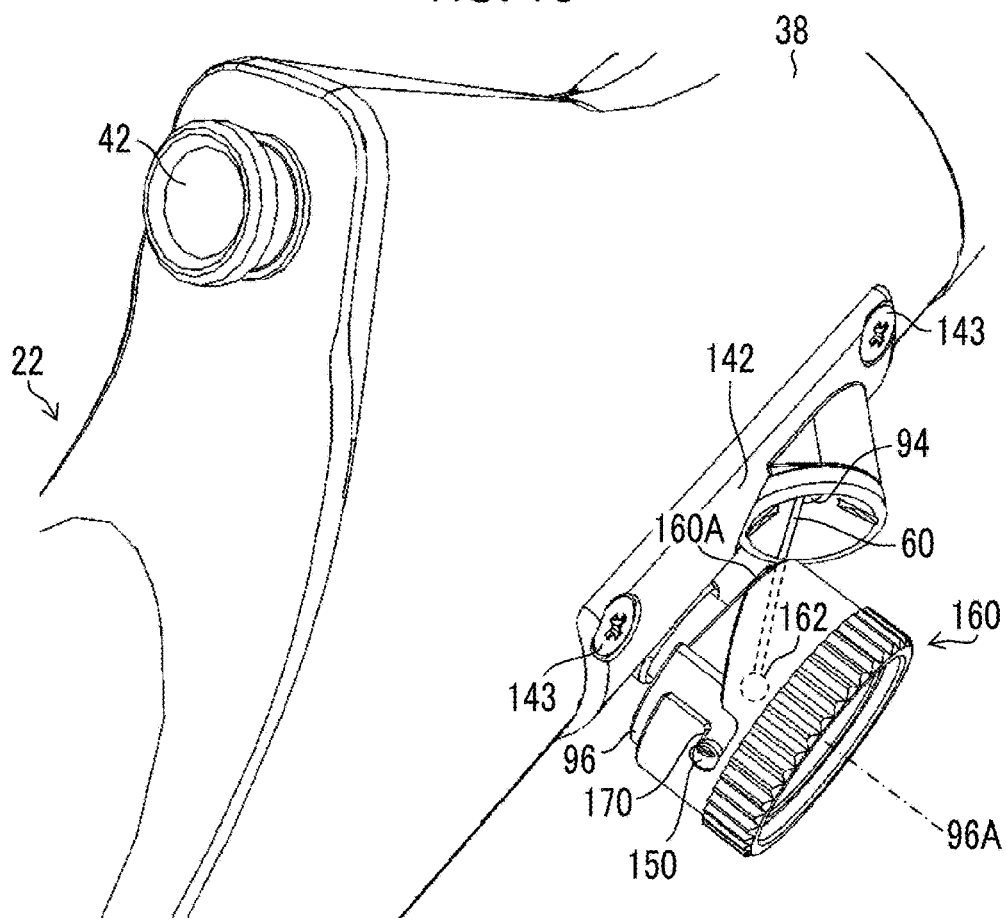
FIG. 18 is a perspective view illustrating a connection structure of a second embodiment.

FIG. 18 is a perspective view illustrating the connection structure of the second embodiment in which the proximal end side of the wire 60 is connected to the rotating member 96. In FIG. 18, the rotating member 96, and a cylindrical cap member 160 are illustrated, and a state where the cap member 160 is mounted on the rotating member 96 is illustrated.

Figure 19:
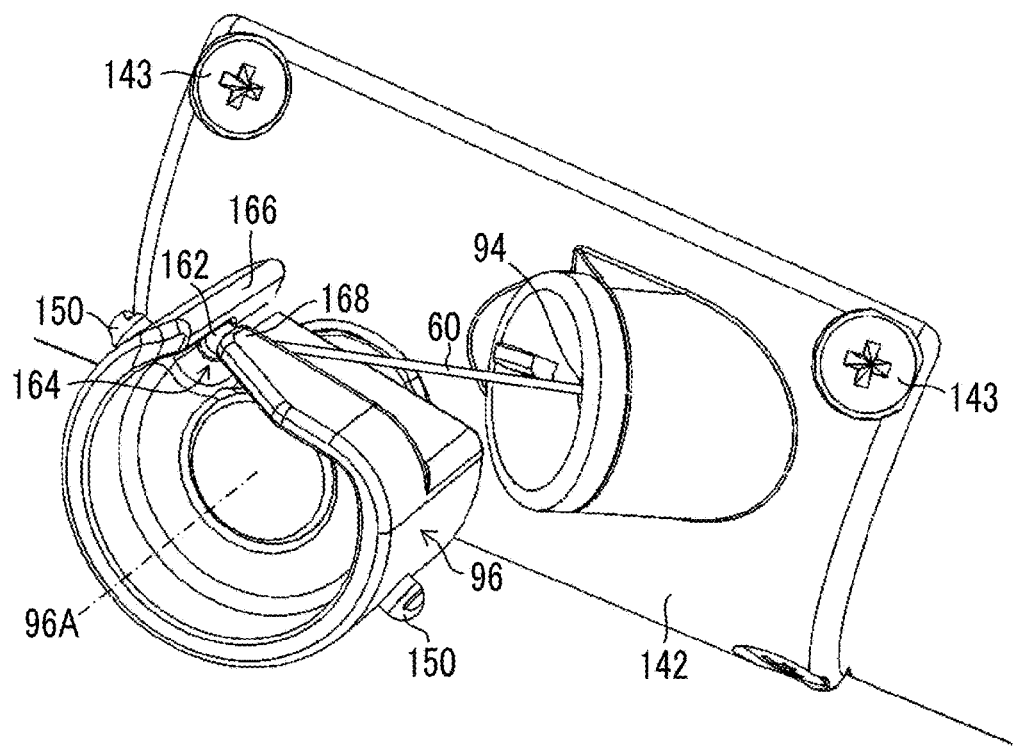
FIG. 19 is an enlarged perspective view in which an engaging part on a distal end side of the wire is engaged with the rotating member.
Figure 20:
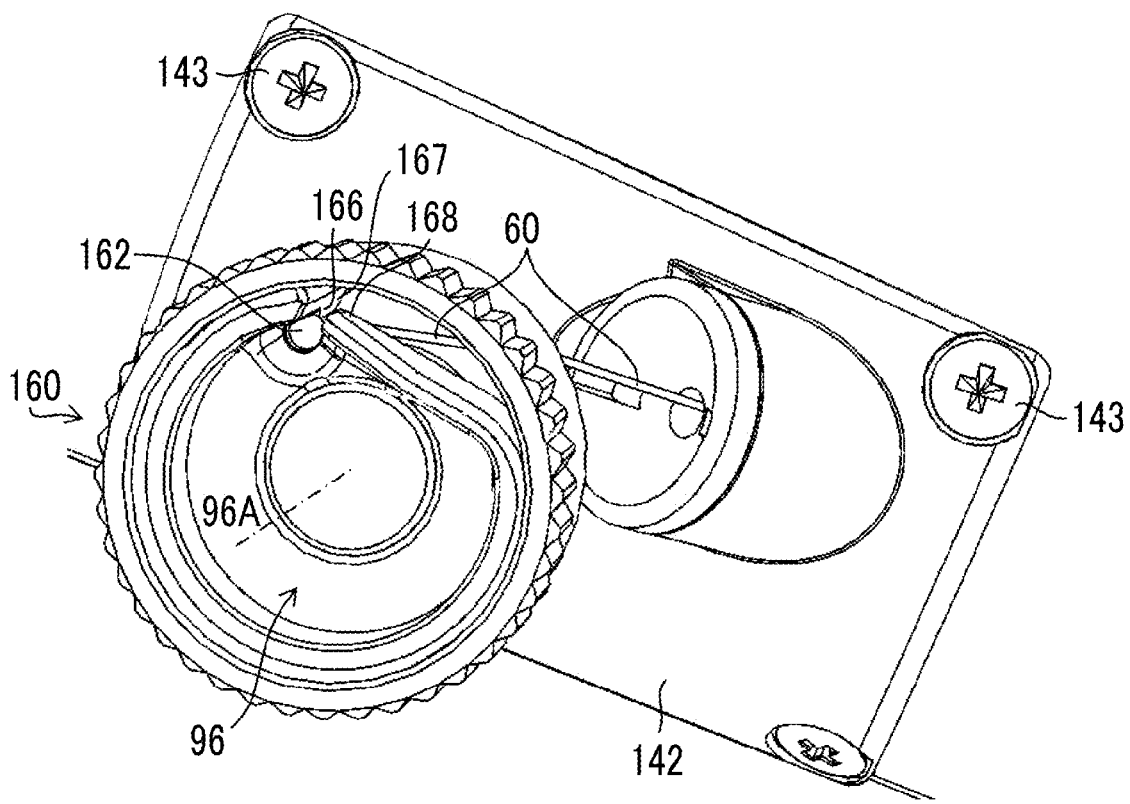
FIG. 20 is an enlarged perspective view in which a cap member is mounted on the rotating member.
Figure 21:
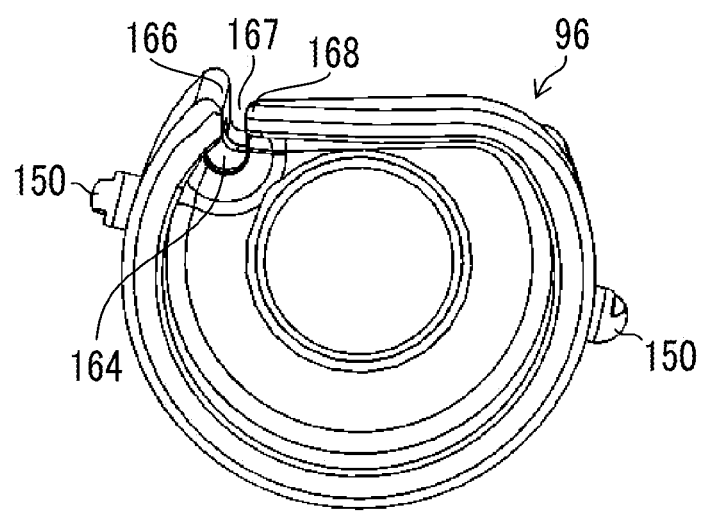
FIG. 21 is an enlarged perspective view of main parts of the rotating member.

Additionally, FIG. 19 is an enlarged perspective view in which an engaging part 162 provided on the distal end side of the wire 60 is engageably and disengageably engaged with an engaged part 164 of the rotating member 96. FIG. 20 is an enlarged perspective view in which the cap member 160 is mounted on the rotating member 96. FIG. 21 is an enlarged perspective view of main parts of the rotating member 96.

As illustrated in FIG. 20, the engaging part 162 is formed in a spherical shape. Additionally, as illustrated in FIG. 21, an outer peripheral part of the rotating member 96 is provided with that a hemispherical engaged part 164 that is engaged with the engaging part 162 (refer to FIG. 20).

The engaged part 164 is surrounded by a wall part 166 and a projection 168 that are formed at the outer peripheral part of the rotating member 96. Additionally, a slit 167 is formed between the wall part 166 and the projection 168. The width of the slit 167 is smaller than the diameter of the engaging part 162 (refer to FIG. 20) and is formed to be larger than the diameter of the wire 60.

In a case where the engaging part 162 is engaged with the engaged part 164, the proximal end side of the wire 60 is inserted from the slit 167 to the engaged part 164 side, and the wire 60 is pulled in a push direction (distal end side of the operating part 22). As a result, the engaging part 162 can be engaged with the engaged part 164. The wall part 166 and the projection 168 prevents the engaging part 162 engaged with the engaged part 164 from slipping out from the engaged part 164.

Additionally, in a case where the engaging part 162 is detached from the engaged part 164, the wire 60 is pulled in a pull direction (the proximal end side of the operating part 22), and the proximal end side of the wire 60 is pulled out via the slit 167 from the engaged part 164 side. As a result, the engaging part 162 can be detached from the engaged part 164. As a result, the engaging part 162 is engageably and disengageably engaged with the engaged part 164.

As illustrated in FIG. 18, in a case where the cap member 160 is mounted on the rotating member 96, an end surface 160A of the cap member 160 on a side that faces the cover 142 abuts against the wire 60. The wire 60 is pressed by the end surface 160A of the cap member 160 abutting against the wire, and a tension is applied to the wire. The engaged state of the engaged part 164 and the engaging part 162 is maintained by this tension. Hence, the cap member 160 can maintain the engaged state between the engaged part 164 and the engaging part 162 by abutting against the wire 60 to applying the tension of the wire 60.

Additionally, the cap member 160 has L-shaped engaging grooves 170 with which the engaging projections 150 of the rotating member 96 attachably and detachably engage. The cap member 160 is switched between a locked position illustrated in FIG. 18 and an unlocked position illustrated in FIG. 22.

Figure 22:
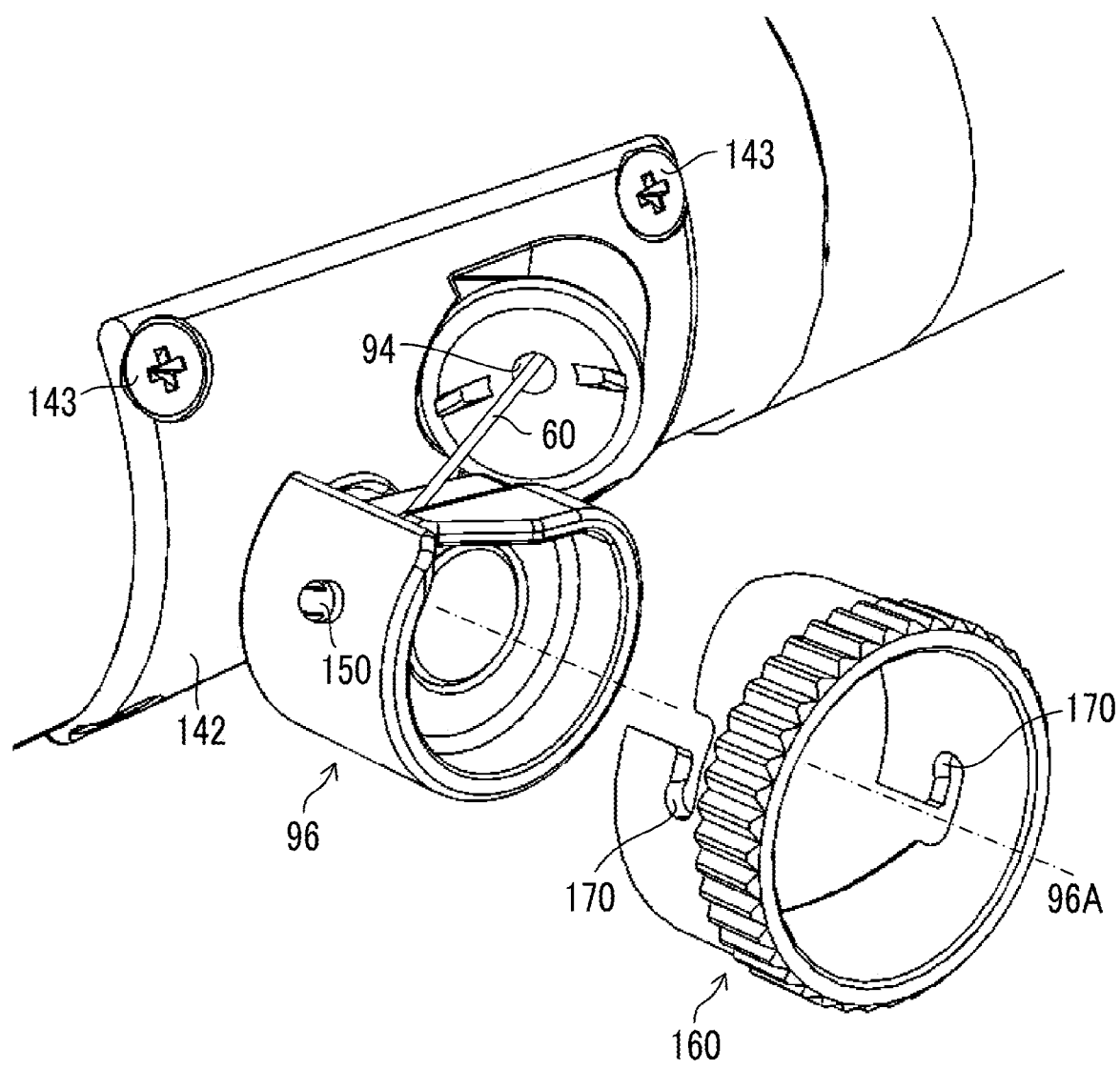
FIG. 22 is an explanatory view of the unlocked position of the connection structure of the second embodiment.

The locked position of FIG. 18 is a position that prevents the slip-out of the cap member 160 from the rotating member 96 by engaging the engaging projection 150 and the engaging groove 170 with each other. The unlocked position of FIG. 22 is a position where the cap member 160 can be detached from the rotating member 96 by releasing the engagement between the engaging projection 150 and the engaging groove 170. In addition, FIG. 22 illustrates that the cap member 160 is separated from the rotating member 96 in order to describe the unlocked position easily.

Next, the connection work of connecting the proximal end side of the wire 60 to the rotating member 96 by the connection structure of the second embodiment will be described.

In this connection work, first, the engaging part 162 is located opposite to the opening part 94 with the engaged part 164 interposed therebetween. Next, the proximal end side of the wire 60 is inserted to the engaged part 164 side via the slit 167 (refer to FIG. 21), and thereafter, the wire 60 is pulled in the push direction and the engaging part 162 is engaged with the engaged part 164. As a result, the proximal end side of the wire 60 can be easily connected to the rotating member 96.

Next, a case where the proximal end side of the wire 60 is detached from the rotating member 96 will be described. First, the cap member 160 is switched to the unlocked position (refer to FIG. 22), and the cap member 160 is detached from the rotating member 96. Next, the wire 60 is pulled in the pull direction, and the proximal end side of the wire 60 is pulled out via the slit 167 from the engaged part 164 side. As a result, the proximal end side of the wire 60 can be easily detached from the rotating member 96. In addition, since the diameter of the engaging part 162 is smaller than the diameter of the wire channel 62, the wire 60 can be pulled out from the distal end part 26. In a case where the wire 60 is pulled out from the distal end part 26 in this way, it is possible to avoid that a body fluid comes out to the operating part 22 side. Thus, the contamination range can be made small.

As described above, according to the connection structure of the second embodiment, similarly to the connection structure of the above-described first embodiment, the attachment and detachment work of the proximal end side of the wire 60 can be easily performed without impairing the operability of the operating part 22.

Additionally, in a case where the cap member 160 is used, the cap member 160 is mounted on the rotating member 96, the cap member 160 is located at the locked position (refer to FIG. 18). As a result, since a state where a tension is applied to the wire 60 by the cap member 160 is maintained, the slip-out of the engaging part 162 from the engaged part 164 can be prevented.

Next, a connection structure of a third embodiment in which the proximal end side of the wire 60 is connected to the rotating member 96 will be described with reference to FIGS. 23, 24, and 25.

In addition, in describing the connection structure of the third embodiment, the same or similar members as those of the connection structure of the second embodiment described in FIGS. 18 to 22 will be designated by the same reference signs and described.

Figure 23:
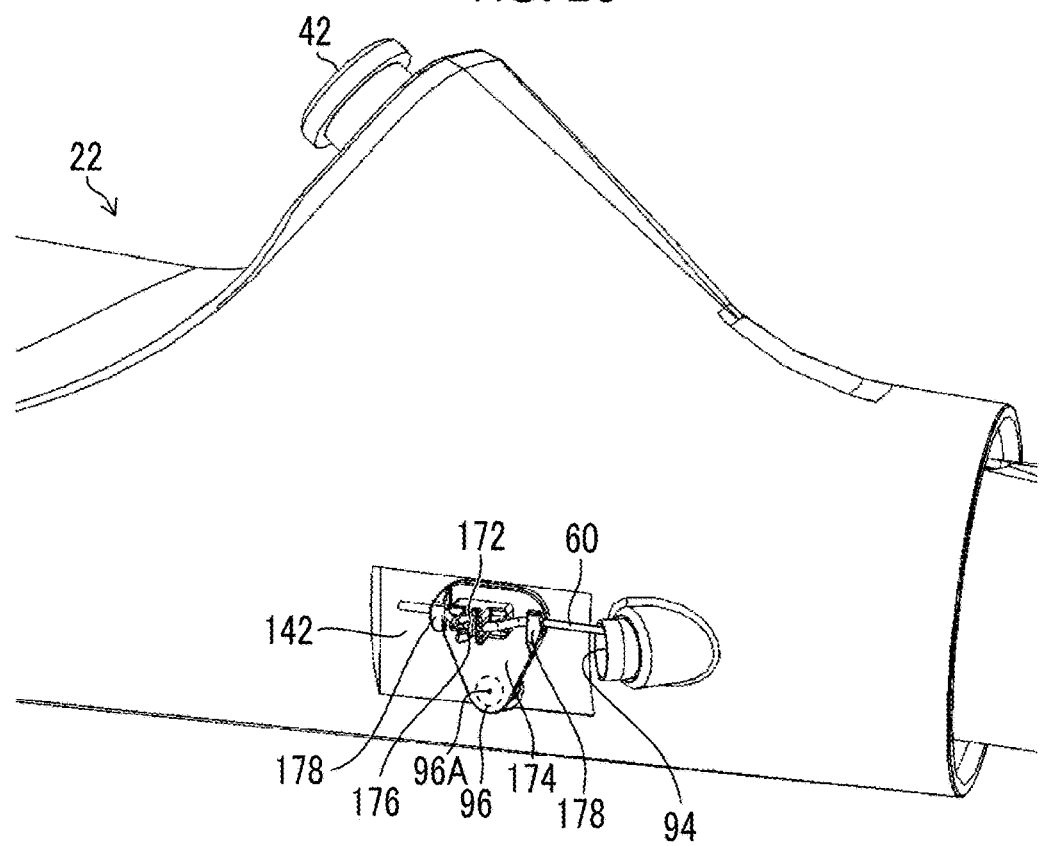
FIG. 23 is a perspective view illustrating a connection structure of a third embodiment.

FIG. 23 is a perspective view illustrating the connection structure of the third embodiment in which the proximal end side of the wire 60 is connected to the rotating member 96. FIG. 24 is an enlarged perspective view of main parts of FIG. 23. FIG. 25 is a perspective view illustrating the internal structure of the rotating member 96 of FIG. 23.

According to the connection structure of the third embodiment, an engaging part 171 is provided on the proximal end side of the wire 60. The engaging part 171 has an engaging piece 172 provided on the proximal end side of the wire 60. The rotating member 96 is provided with an engaged part 174. This engaged part 174 has an engaging recess 176 with which the engaging piece 172 engages, and engaging claws 178 and 178 which are disposed on both sides of the engaging recess 176 and which the wire 60 engages.

Figure 24:
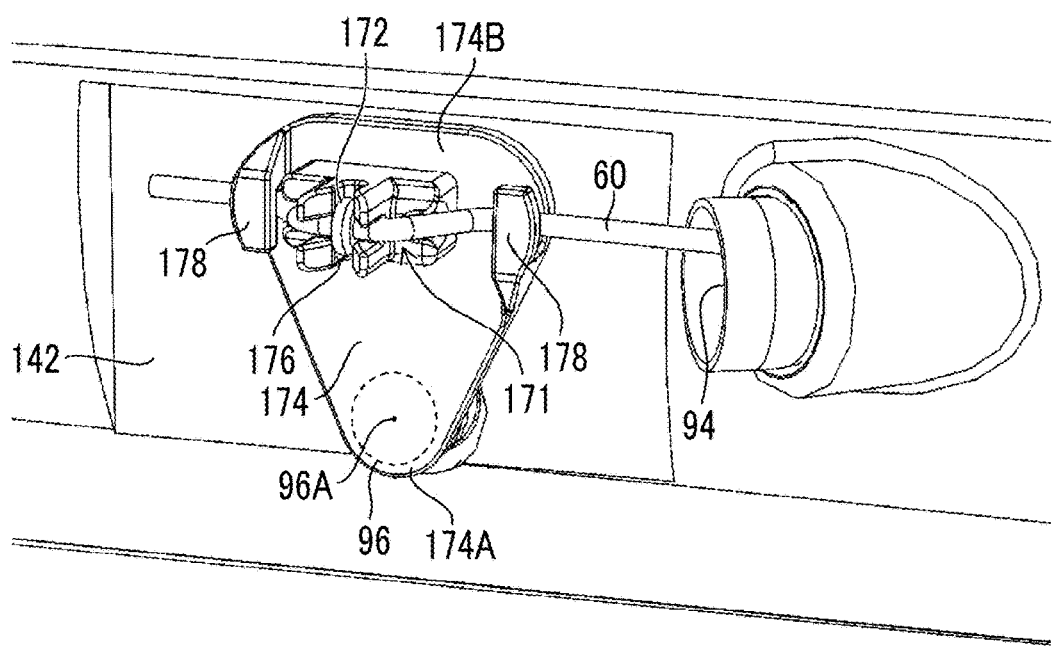
FIG. 24 is an enlarged perspective view of main parts of FIG. 23.

As illustrated in FIG. 24, the engaged part 174 is formed in a triangular shape in a plan view, and an apex angle portion 174A thereof is coupled to the rotating member 96. The engaging recess 176 and the engaging claws 178 and 178 are provided along a base at a base portion 174B of the engaged part 174. That is, the engaging recess 176 and the engaging claws 178 and 178 are disposed at positions offset from each other in a direction orthogonal to the rotational axis 96A from the rotational axis 96A.

Figure 25:
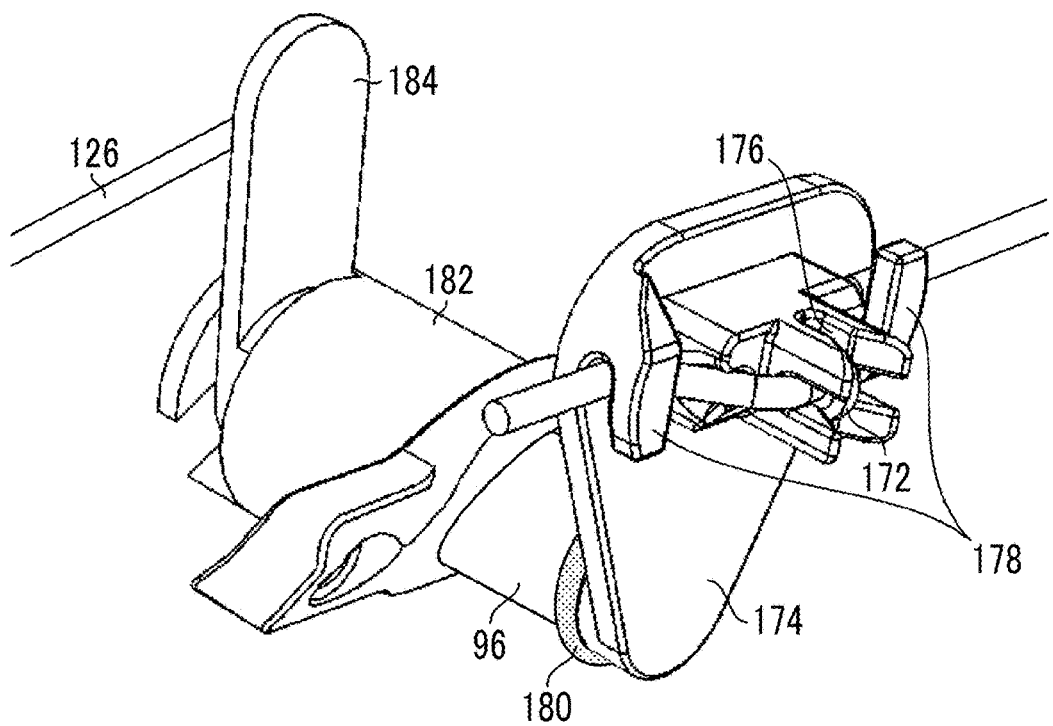
FIG. 25 is a perspective view illustrating the internal structure of a rotating member of FIG. 23.

As illustrated in FIG. 25, an O-ring 180 is attached to the rotating member 96 and is rotatably supported by an opening part (not illustrated) of the cover 142 (refer to FIG. 24) via the O-ring 180. Additionally, the rotating member 96 is rotatably supported by the bearing part 182 inside the operating part 22. Moreover, the lever 184 is attached to an end part of the rotating member 96, and the wire 126 is coupled to an end part of this lever 184. Hence, the rotating member 96 is rotationally operated via the lever 184 by the push/pull operation of the wire 126.

Next, the connection work of connecting the proximal end side of the wire 60 to the rotating member 96 by the connection structure of the third embodiment will be described.

In this connection work, first, the engaging part 171 of the wire 60 is located at the engaged part 174. Next, the engaging piece 172 is engaged with the engaging recess 176, and thereafter, the wire 60 is engaged with the engaging claws 178 and 178. The proximal end side of the wire 60 can be easily connected to the rotating member 96 by this work.

Additionally, as an example of the other connection work, the wire 60 may be engaged with one engaging claw 178, the engaging piece 172 may be engaged with the engaging recess 176, and thereafter, the wire 60 may be engaged with the other engaging claw 178.

Next, a case where the proximal end side of the wire 60 is detached from the rotating member 96 will be described. First, the wire 60 is detached from the engaging claws 178 and 178, and thereafter the engaging piece 172 is detached from the engaging recess 176. The proximal end side of the wire 60 can be easily detached from the rotating member 96 by this work. In addition, since the diameter of the engaging piece 172 is smaller than the diameter of the wire channel 62, the wire 60 can be pulled out from the distal end part 26. In a case where the wire 60 is pulled out from the distal end part 26 in this way, it is possible to avoid that a body fluid comes out to the operating part 22 side. Thus, the contamination range can be made small.

As described above, according to the connection structure of the third embodiment, similarly to the connection structures of the above-described embodiments, the attachment and detachment work of the proximal end side of the wire 60 can be easily performed without impairing the operability of the operating part 22.

In addition, in the connection structure of the third embodiment, the engaging claws 178 and 178 are disposed on both sides of the engaging recess 176. However, the invention is not limited to this. For example, an engaging claw may be disposed on one side of the engaging recess 176. Additionally, the number of engaging claws 178 is not limited to two, and one or more engaging claws 178 may be provided.

Next, a connection structure of a fourth embodiment in which the proximal end side of the wire 60 is connected to the rotating member 96 will be described with reference to FIGS. 26 to 30.

In addition, in describing the connection structure of the fourth embodiment, the same or similar members as those of the connection structure of the third embodiment described in FIGS. 23 to 25 will be designated by the same reference signs and described.

Figure 26:
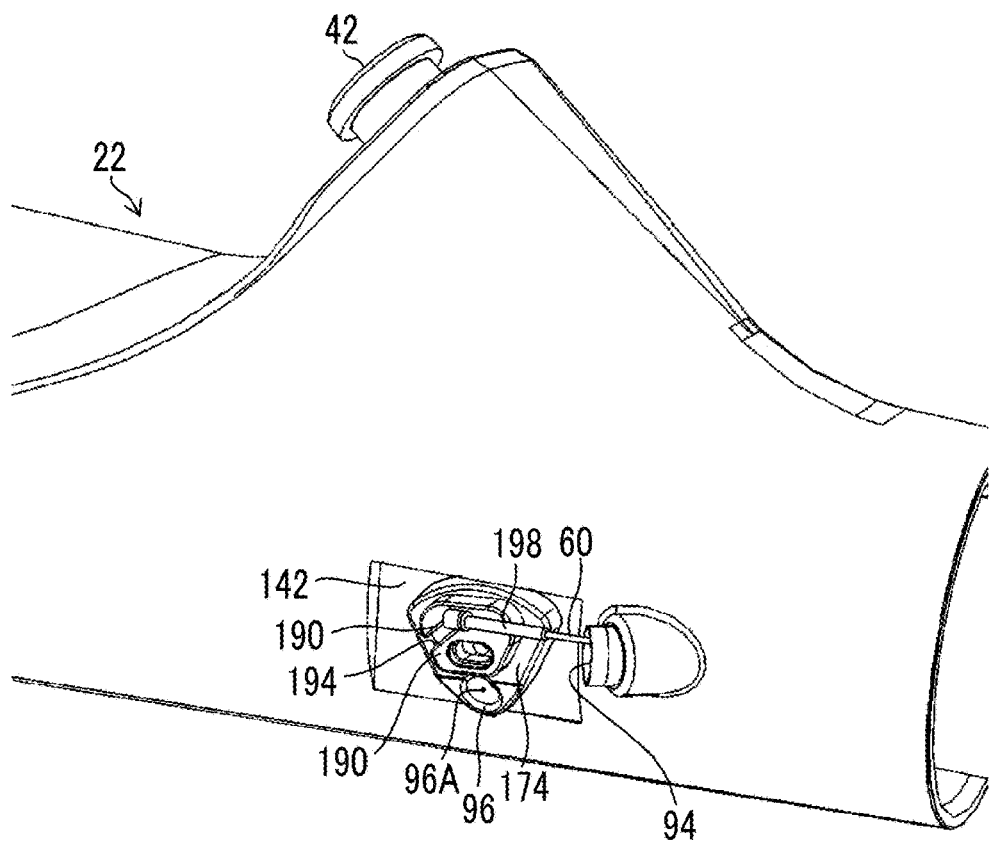
FIG. 26 is a perspective view illustrating a connection structure of a fourth embodiment.
Figure 27:
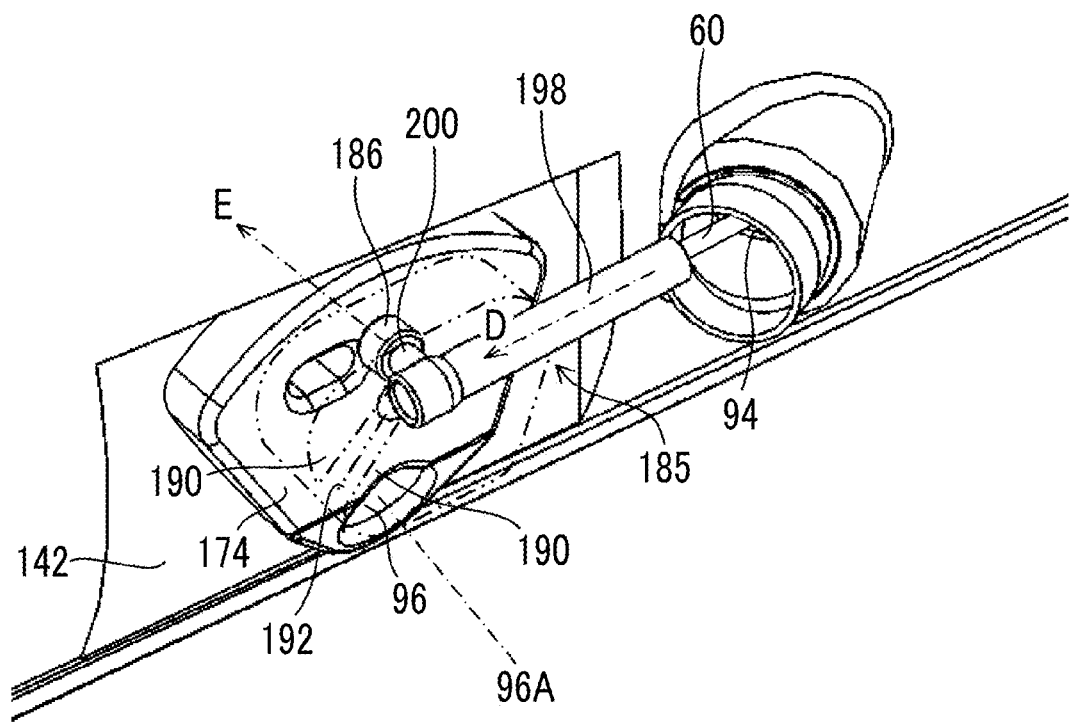
FIG. 27 is an enlarged perspective view of main parts of FIG. 26.
Figure 28:
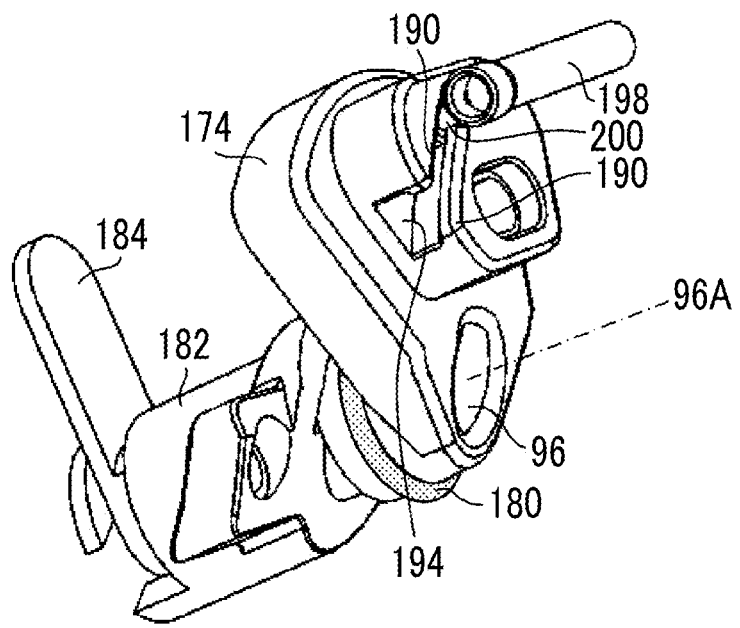
FIG. 28 is a perspective view illustrating the internal structure of a rotating member of FIG. 26.
Figure 29:
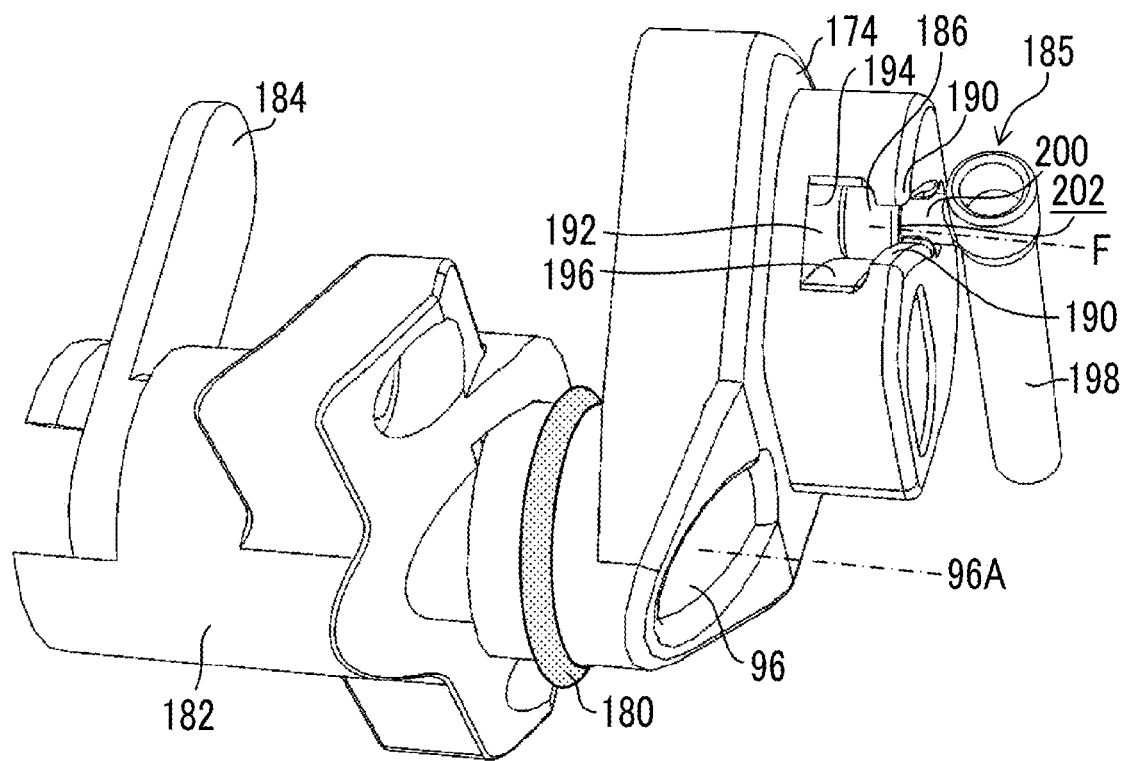
FIG. 29 is a perspective view illustrating the internal structure of a rotating member of FIG. 26.
Figure 30:
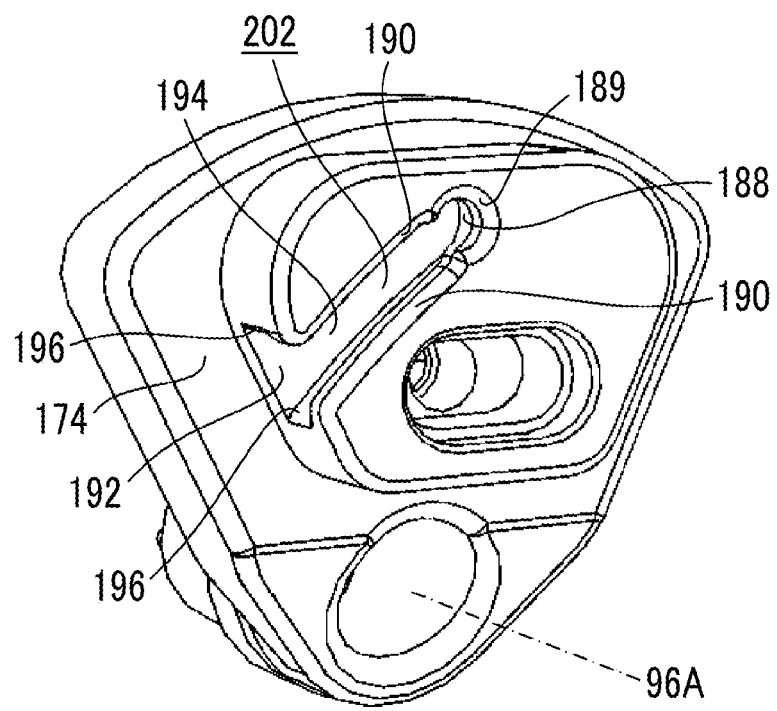
FIG. 30 is an enlarged view of the rotating member of FIG. 26.

FIG. 26 is a perspective view illustrating the connection structure of the fourth embodiment in which the proximal end side of the wire 60 is connected to the rotating member 96. FIG. 27 is an enlarged perspective view of main parts of FIG. 26 and illustrates a portion of the engaged part 174 with a two-dot chain line. FIG. 28 is a perspective view illustrating the internal structure of the rotating member 96 of FIG. 26. FIG. 29 is a perspective view illustrating the internal structure of the rotating member 96 as seen from a different angle with respect to FIG. 28. FIG. 30 is an enlarged perspective view of the rotating member 96 of FIG. 26.

According to the connection structure of the fourth embodiment as illustrated in FIGS. 27 and 29, an engaging part 185 is provided on the proximal end side of the wire 60. The engaging part 185 has an engaging piece 186 provided on the proximal end side of the wire 60.

As illustrated in FIG. 30, The engaged part 174 of the rotating member 96 has an engaging recess 188 with which the engaging piece 186 (refer to FIG. 29) engages, a restricting part 189 that restricts the engaging piece 186 from slipping out in the direction (a direction of arrow F: refer to FIG. 29) parallel to the rotational axis 96A from the engaging recess 188, and an opening part 192 that is continuously connected to the engaging recess 188 for attachably and detachably engaging the engaging piece 186 with the engaging recess 188. As illustrated in FIG. 30, the engaging recess 188 is disposed at a position offset in a direction orthogonal to the rotational axis 96A from the rotational axis 96A.

The engaged part 174 has a passage 194 ranging from the opening part 192 to the engaging recess 188. The passage 194 is formed between a pair of wall parts 196 and 196 that faces each other. Restricting parts 190 and 190 are formed in the wall parts 196 and 196.

As illustrated in FIG. 27, the engaging piece 186 is formed in a columnar shape. Additionally, the engaging piece 186 is provided via a shaft 200 at a proximal end of an engaging piece holding member 198. The engaging piece holding member 198 is formed in a tube shape and covers the proximal end side of the wire 60. The shaft 200 extends in a direction (a direction of arrow E) orthogonal to an axial direction (a direction of arrow D) of the wire 60 from the engaging piece holding member 198. As a result, the engaging piece 186 is disposed at a position offset in the direction (the direction of arrow E) orthogonal to the axial direction (the direction of arrow D) of the wire 60 from the wire 60.

Additionally, in a case where the engaging piece 186 is engaged with the engaging recess 188, as illustrated in FIG. 30, the shaft 200, is inserted through a slit 202 between the pair of restricting parts 190 and 190 that faces each other. The width of the slit 202 is formed to be larger than the diameter of the shaft 200 and smaller than the diameter of the engaging piece 186. As a result, the engaging piece 186 located in the passage 194 is restricted from slipping out in the direction (the direction of arrow F) parallel to the rotational axis 96A from the slit 202.

Additionally, the restricting part 189 is formed in a circular-arc shape. The diameter of the restricting part 189 is formed to be larger than the diameter of the shaft 200 and smaller than the diameter of the engaging piece 186. As a result, as illustrated in FIG. 29, the engaging piece 186 is restricted from slipping out in the direction (the direction of arrow F) parallel to the rotational axis 96A from the engaging recess 188.

Next, the connection work of connecting the proximal end side of the wire 60 to the rotating member 96 by the connection structure of the fourth embodiment will be described.

In this connection work, the engaging piece 186 provided on the proximal end side of the wire 60 is inserted into the passage 194 from the opening part 192 of the engaged part 174, is passed through the passage 194, and is engaged with the engaging recess 188. The proximal end side of the wire 60 can be easily connected to the rotating member 96 by this work.

Next, in a case where the proximal end side of the wire 60 is detached from the rotating member 96, the engaging piece 186 is detached from the passage 194 via the engaging recess 188 from the opening part 192. The proximal end side of the wire 60 can be easily detached from the rotating member 96 by this work.

As described above, according to the connection structure of the fourth embodiment, similarly to the connection structures of the above-described embodiments, the attachment and detachment work of the proximal end side of the wire 60 can be easily performed without impairing the operability of the operating part 22.

Next, a connection structure of a fifth embodiment in which the proximal end side of the wire 60 is connected to the rotating member 96 will be described.

In addition, in describing the connection structure of the fifth embodiment, the same or similar members as those of the connection structure of the fourth embodiment described in FIGS. 26 to 30 will be designated by the same reference signs and described.

Figure 31:
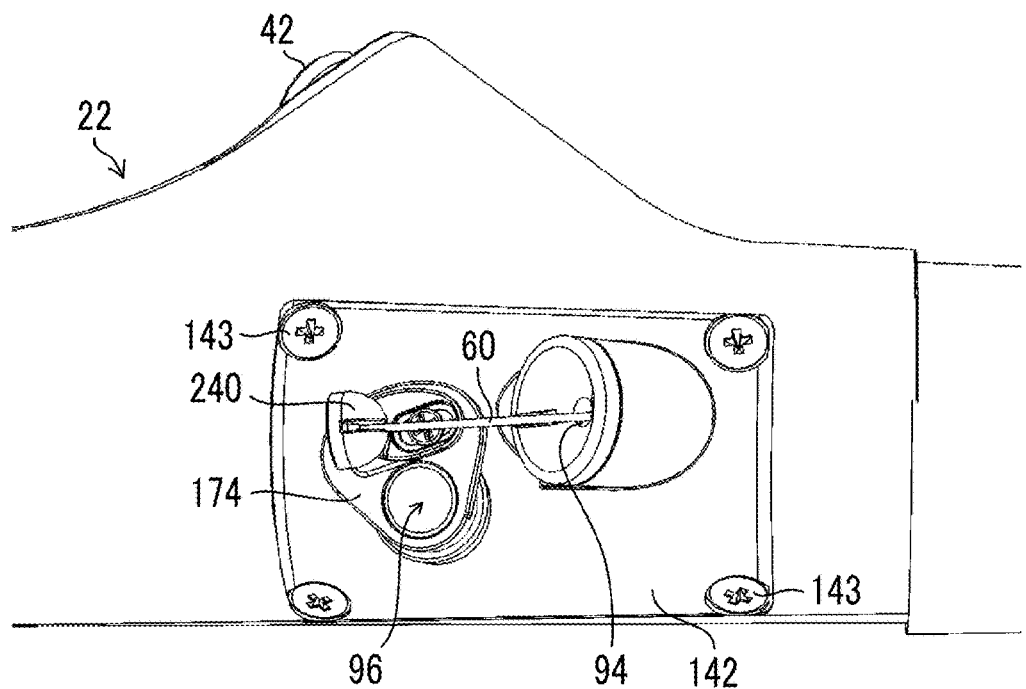
FIG. 31 is an overall perspective view illustrating a connection structure of a fifth embodiment.
Figure 32:
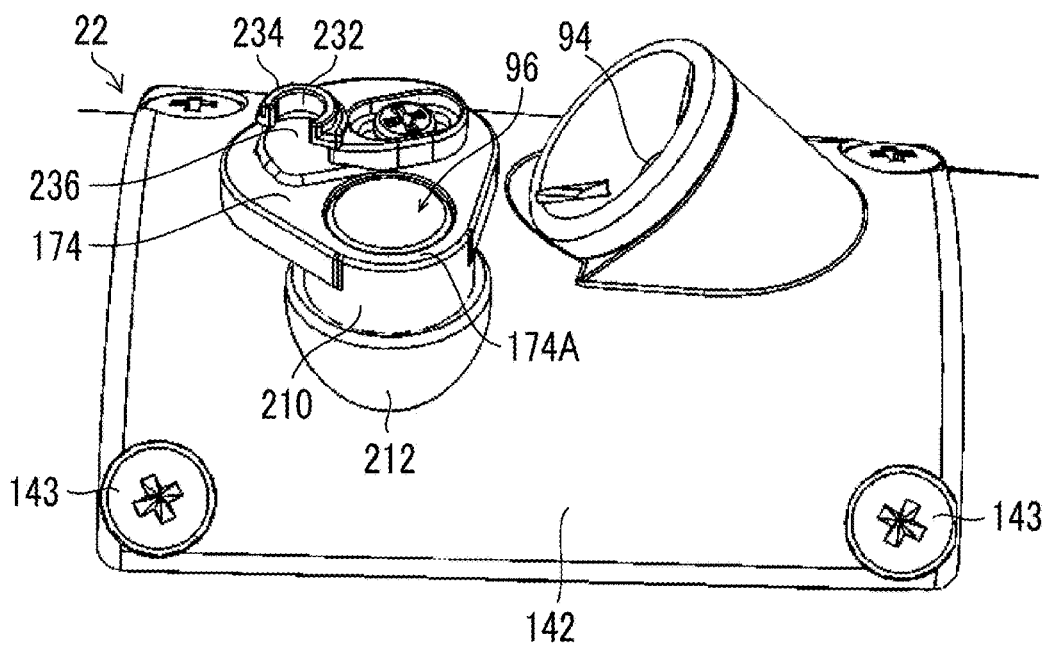
FIG. 32 is a perspective view of the connection structure as seen from a different angle with respect to FIG. 31.
Figure 33:
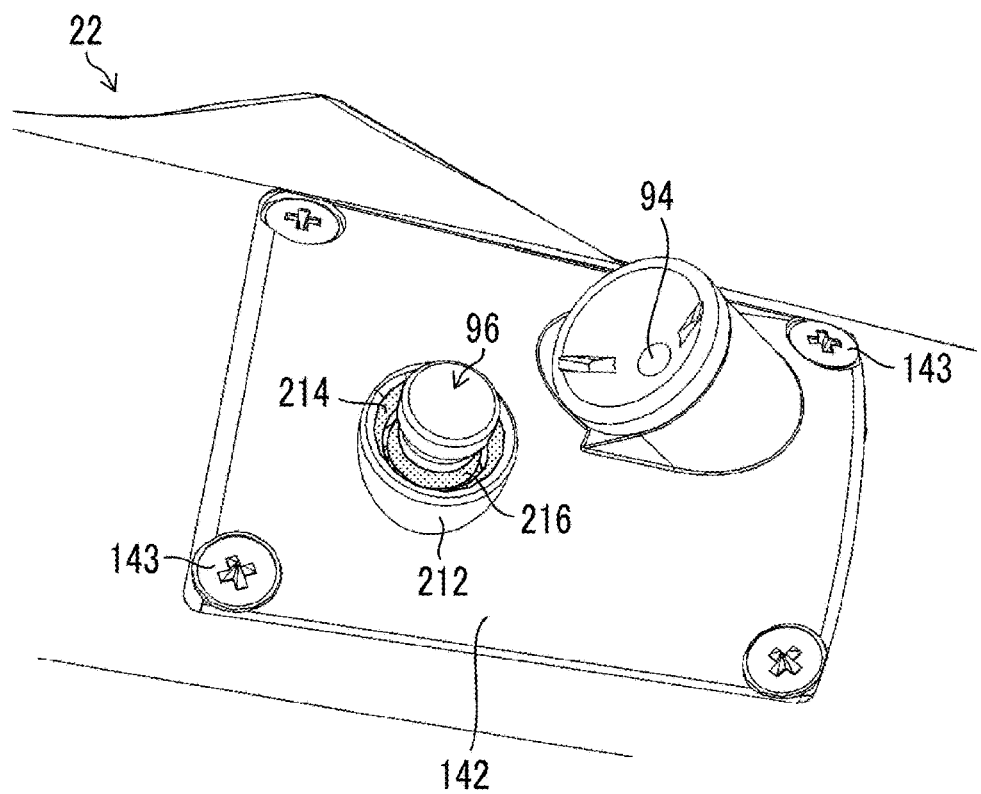
FIG. 33 is a perspective view of a connection structure in which an engaged part is detached from the connection structure of FIG. 31.
Figure 34:
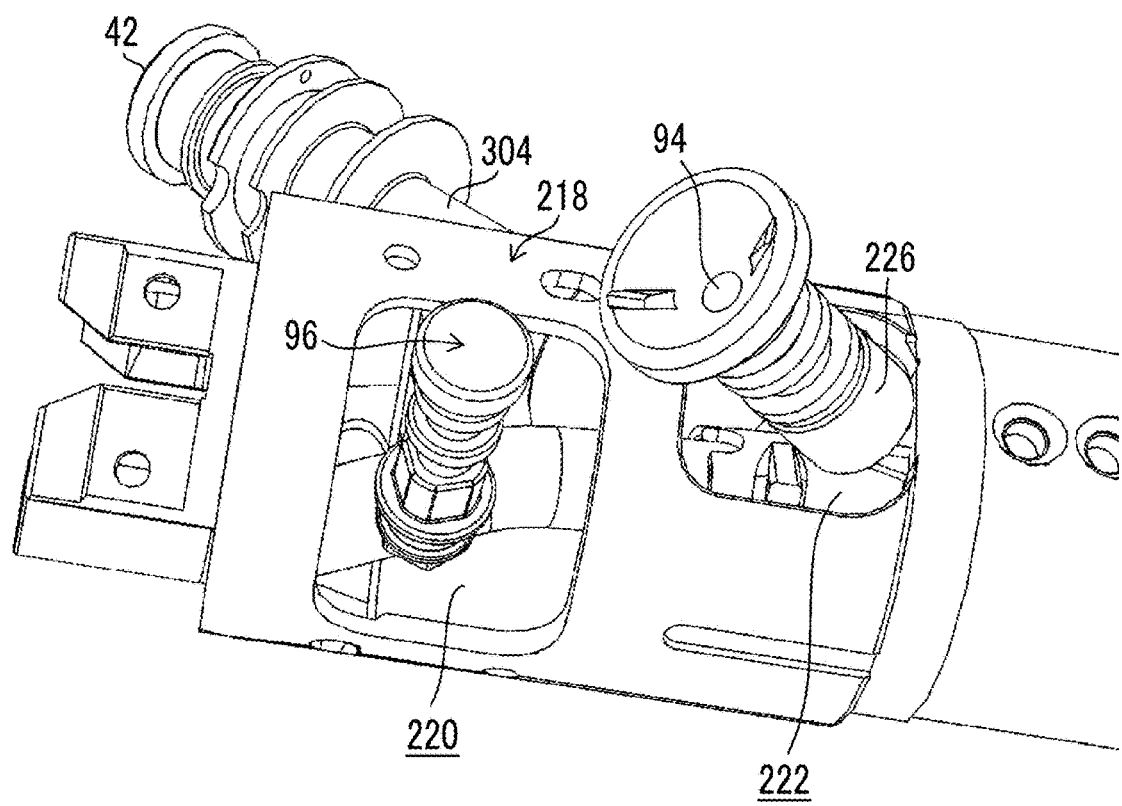
FIG. 34 is a perspective view illustrating the internal structure of the connection structure of FIG. 33.
Figure 35:
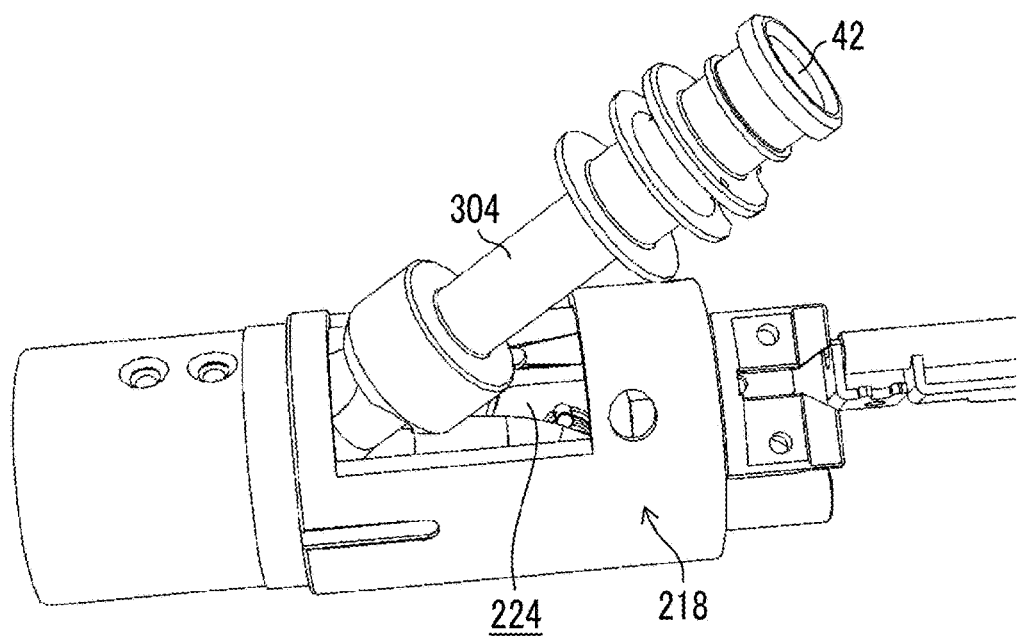
FIG. 35 is a perspective view of the internal structure as seen from a different angle with respect to FIG. 34.
Figure 36:
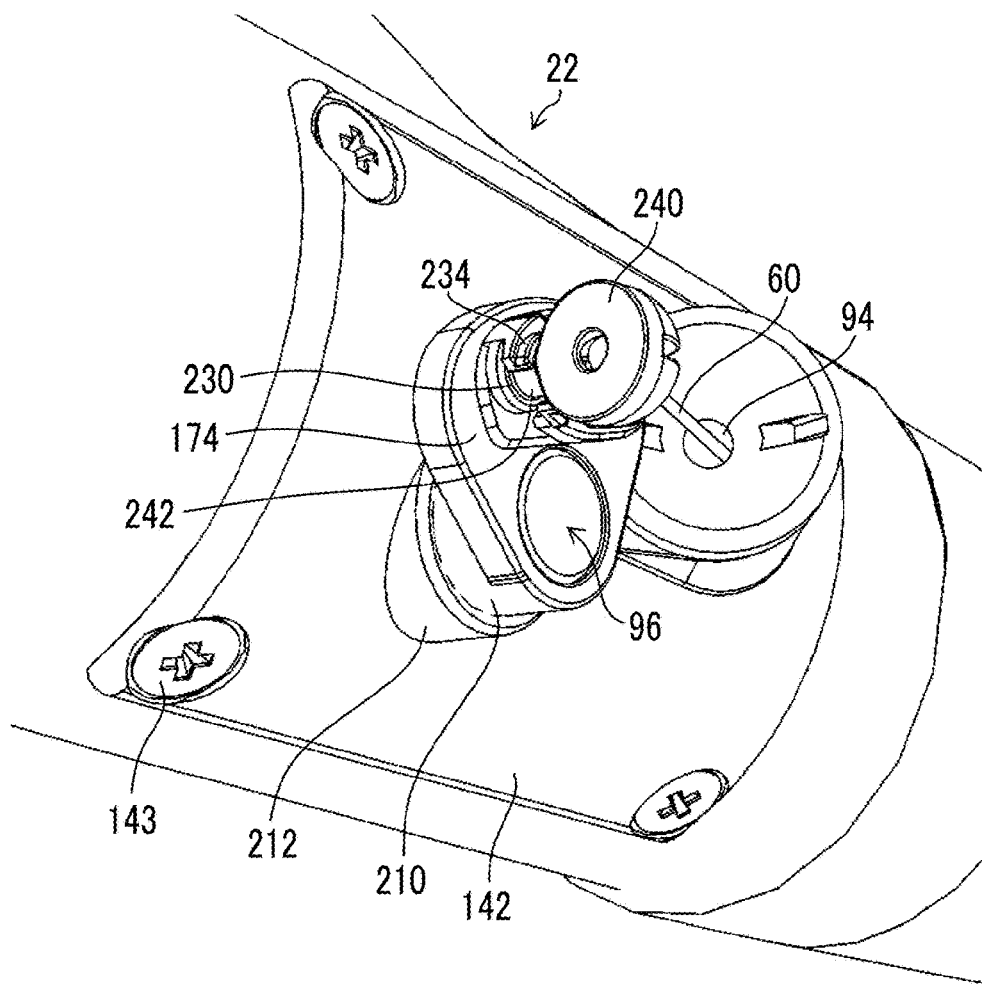
FIG. 36 is an enlarged perspective view of main parts illustrating the connection structure of the fifth embodiment.
Figure 37:
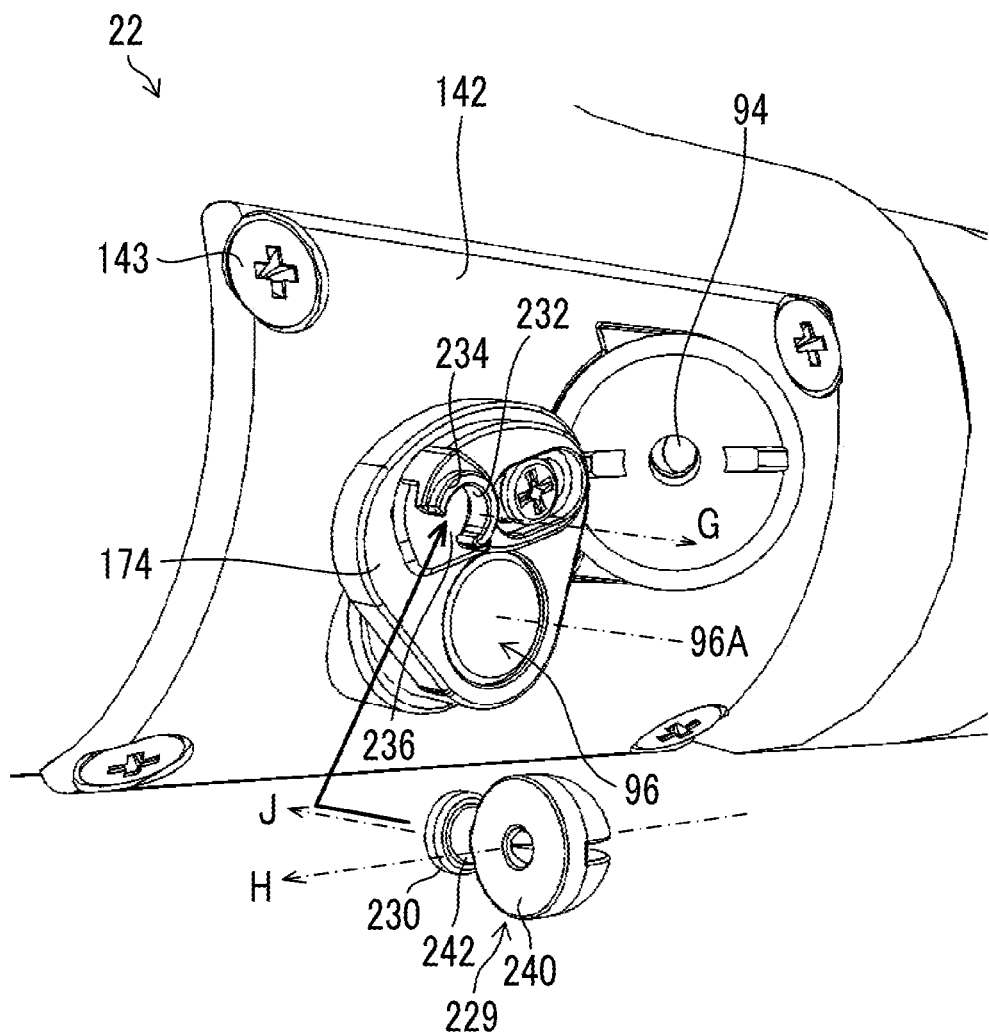
FIG. 37 is an assembling perspective view of main parts of FIG. 36.

FIG. 31 is an overall perspective view illustrating the connection structure of the fifth embodiment in which the proximal end side of the wire 60 is connected to the rotating member 96. FIG. 32 is a perspective view of the connection structure of FIG. 31 as seen from a different angle with respect to FIG. 31, and illustrates a portion of a structure including the wire 60 in an omitted manner. FIG. 33 is a perspective view of a connection structure in which an engaged part 174 is detached from the connection structure of FIG. 31. FIG. 34 is a perspective view illustrating the internal structure of the connection structure of FIG. 33. FIG. 35 is a perspective view of the internal structure as seen from a different angle with respect to FIG. 34. A detailed structure of the connection structure of the fifth embodiment is illustrated in FIGS. 36 and 37. FIGS. 36 and 37 will be described below.

As illustrated in FIG. 32, a cylindrical part 210 is provided in the apex angle portion 174A of the engaged part 174. The rotating member 96 is fitted into the cylindrical part 210. As a result, the engaged part 174 is coupled to the rotating member 96. The cylindrical part 210 is rotatably supported by a boss (sleeve) part 212 formed in the cover 142. As a result, the rotating member 96 is rotatably supported by the cover 142 via the cylindrical part 210.

Additionally, an outer peripheral surface of the cylindrical part 210 is attached to an inner peripheral surface of the boss part 212 via an O-ring 214 illustrated in FIG. 33. As a result, the watertightness between the cylindrical part 210 and the boss part 212 is held by the O-ring 214. Additionally, the outer peripheral surface of the rotating member 96 is attached to an inner peripheral surface of the cylindrical part 210 (refer to FIG. 32) via an O-ring 216. As a result, the watertightness between the cylindrical part 210 and the rotating member 96 is held by the O-ring 216.

As illustrated in FIGS. 34 and 35, a tubular frame 218 is provided inside the operating part 22. Rectangular opening parts 220, 222, and 224 are formed in the frame 218. The rotating member 96 is disposed to protrude from the opening part 220 toward the outside, an introduction tube 226 is disposed to protrude from the opening part 222 toward the outside, and a pipe line 304 is disposed to protrude from the opening part 224 toward the outside. The introduction tube 226 of FIG. 34 has the opening part 94 formed at a proximal end thereof and has the proximal end of the wire channel 62 (refer to FIG. 2) connected at a distal end thereof.

Next, the connection structure of the fifth embodiment will be described with reference to FIGS. 36 and 37.

FIG. 36 is an enlarged perspective view of main parts illustrating the connection structure of the fifth embodiment. FIG. 37 is an assembling perspective view of the main parts of FIG. 36.

According to the connection structure of the fifth embodiment, an engaging part 229 is provided on the proximal end side of the wire 60. The engaging part 229 has an engaging piece 230 provided on the proximal end side of the wire 60.

The rotating member 96 is provided with an engaged part 174. As illustrated in FIG. 37, the engaged part 174 has an engaging recess 232 with which the engaging piece 230 engages, a restricting part 234 that restricts the engaging piece 230 from slipping out in the direction (a direction of arrow G) parallel to the rotational axis 96A from the engaging recess 232, and an opening part 236 that is continuously connected to the engaging recess 232 for attachably and detachably engaging the engaging piece 230 with the engaging recess 232. Additionally, the engaging recess 232 is disposed at the position offset in the direction orthogonal to the rotational axis 96A from the rotational axis 96A.

The engaging piece 230 is formed in a disk shape. Additionally, the engaging piece 230 is provided via a shaft 242 at the engaging piece holding member 240. The engaging piece holding member 240 is formed in a hemispherical shape and is attached to the proximal end of the wire 60. The shaft 242 extends in a direction (a direction of arrow J) orthogonal to an axial direction (a direction of arrow H) of the wire 60 from the engaging piece holding member 240. As a result, the engaging piece 230 is disposed at a position offset in the direction (the direction of arrow J) orthogonal to the axial direction (the direction of arrow H) of the wire 60 from the wire 60.

Additionally, in a case where the engaging piece 230 is engaged with the engaging recess 232, the engaging piece 230 is engaged with the engaging recess 232 from the opening part 236. In this engaged state, as illustrated in FIG. 37, the shaft 242 is inserted through the restricting part 234 formed in a circular-arc shape. The diameter of the restricting part 234 is formed to be larger than the diameter of the shaft 242 and smaller than the diameter of the engaging piece 230. As a result, the engaging piece 230 is restricted from slipping out in the direction (the direction of arrow G) parallel to the rotational axis 96A from the engaging recess 232.

Next, the connection work of connecting the proximal end side of the wire 60 to the rotating member 96 by the connection structure of the fifth embodiment will be described.

In this connection work, the engaging piece 230 provided on the proximal end side of the wire 60 is engaged with the engaging recess 232 from the opening part 236 of the engaged part 174. The proximal end side of the wire 60 can be easily connected to the rotating member 96 by this work.

Additionally, in a case where the proximal end side of the wire 60 is detached from the rotating member 96, the engaging piece 230 engaged with the engaging recess 232 is detached from the opening part 236. The proximal end side of the wire 60 can be easily detached from the rotating member 96 by this work.

As described above, according to the connection structure of the fifth embodiment, similarly to the connection structures of the above-described embodiments, the attachment and detachment work of the proximal end side of the wire 60 can be easily performed without impairing the operability of the operating part 22.

In the above-described first to fifth embodiments, the duodenoscope has been exemplified and described as the endoscope 10. However, as long as an endoscope comprising an elevator for adjusting the delivery direction of a treatment tool at a distal end part of an insertion part is provided, the invention can be applied to various endoscopes, such as an ultrasonic endoscope.

EXPLANATION OF REFERENCES

- 10: endoscope
- 12: endoscope system
- 14: processor device
- 16: light source device
- 18: display
- 20: erection operating lever
- 22: operating part
- 23: opening part
- 24: insertion part
- 26: distal end part
- 28: distal end member
- 28A: peripheral surface
- 30: elevator
- 30A: guide surface
- 30B: proximal part
- 32: operating part body
- 34: gripping part
- 38: folding-preventing tube
- 38A: proximal end part
- 42: treatment tool introduction port
- 46: universal cord
- 48: electric connector
- 50: light source connector
- 52: bending part
- 54: flexible part
- 56: treatment tool
- 56A: distal end part
- 58: treatment tool channel
- 60: wire
- 62: wire channel
- 64: angle knob
- 66: air/water supply button
- 68: suction button
- 70: air/water supply nozzle
- 72: treatment tool delivery port
- 74: delivery port
- 76: cap
- 76A: opening window
- 78: partition wall
- 78A: bearing part
- 80: partition wall
- 80A: bearing part
- 82: elevator housing chamber
- 84: rotational movement shaft
- 86: rotational movement shaft
- 88: optical system housing chamber
- 90: illumination window
- 92: observation window
- 94: opening part
- 96: rotating member
- 96A: rotational axis
- 96B proximal part
- 100: engaging member
- 102: housing groove
- 104: opening
- 106: engagement guide part
- 108: engagement guide path
- 110: deformation generating part
- 112: groove
- 114: groove
- 116: separation guide surface
- 120: erection operating mechanism
- 124: arm
- 126: wire
- 126A: wire engaging part
- 128: rotational driving unit
- 128A: opening part
- 128B: wire engaged part
- 130: housing space
- 132: bearing part
- 140: locking member
- 142: cover
- 143: screw
- 144: engaged part
- 146: rotation restricting part
- 148: rotation restricting part
- 150: engaging projection
- 152: engaging groove
- 160: cap member
- 160A: end surface
- 162: engaging part
- 164: engaged part
- 166: wall part
- 168: projection
- 170: engaging groove
- 171: engaging part
- 172: engaging piece
- 174: engaged part
- 174A: apex angle portion
- 174B: base portion
- 176: engaging recess
- 178: engaging claw
- 180: O-ring
- 182: bearing part
- 184: lever
- 185: engaging part
- 186: engaging piece
- 188: engaging recess
- 189: restricting part
- 190: restricting part
- 192: opening part
- 194: passage
- 196: wall part
- 198: engaging piece holding member
- 200: shaft
- 202: slit
- 210: cylindrical part
- 212: boss part
- 214: O-ring
- 216: O-ring
- 218: frame
- 220: opening part
- 222: opening part
- 224: opening part
- 226: introduction tube
- 229: engaging part
- 230: engaging piece
- 232: engaging recess
- 234: restricting part
- 236: opening part
- 240: engaging piece holding member 242: shaft
300: branched tube
302: distal end tube
304: pipe line
306: pipe line

What is claimed is:

1. An endoscope comprising:
   an operating part, comprising a shell, that is provided with an operating member disposed on an outside of the shell;
   an insertion part that is provided on a distal end side of the operating part and is inserted into a subject;
   an elevator that is provided at a distal end part of the insertion part;
   an erection operating wire that is disposed to be inserted into a wire insertion passage formed from the operating part to the insertion part so as to be movable forward and backward and is attachably and detachably coupled to the elevator on a distal end side thereof;
   an opening part that is provided at a proximal end of the wire insertion passage and delivers a proximal end side of the erection operating wire to the outside of the shell;
   a rotating member, comprising a surface, that is disposed to be exposed to the outside of the shell and is configured to be rotatable around a rotational axis having a component in a direction orthogonal to a longitudinal direction of the operating part depending on the operation of the operating member;
   an engaged part that is provided in the rotating member; and
   an engaging part that is provided on the proximal end side of the erection operating wire and is engageably and disengageably engageable with the engaged part,
   wherein the operating part includes angle knobs configured to be rotationally operated around a knob rotational axis to bend the insertion part, and
   wherein the rotational axis of the rotating member is an axis different from the knob rotational axis,
   wherein the wire insertion passage is disposed on an inside of the shell;
   further comprising: a cap that is attachably and detachably mountable on the rotating member and maintains an engaged state between the engaged part and the engaging part by abutting against the erection operating wire to apply a tension.

2. The endoscope according to claim 1, further comprising:
   a locking member that is attachably and detachably mountable on the rotating member and is switchable between a locked position where release of an engaged state between the engaged part and the engaging part is prevented and an unlocked position where the release of the engaged state between the engaged part and the engaging part is allowed.

3. The endoscope according to claim 2,
   wherein the rotating member has an engaging projection, and
   wherein the locking member has an engaging groove with which the engaging projection attachably and detachably engages and which is switchable between a locked position where the engaging projection and the engaging groove engage with each other and an unlocked position where the engagement between the engaging projection and the engaging groove is released.

4. The endoscope according to claim 1,
   wherein the engaged part has a rotation restricting part that restricts relative rotation of the engaging part with respect to the engaged part.

5. The endoscope according to claim 4,
   wherein the rotation restricting part has a D-cut rotation restricting surface that is formed in the engaged part.

6. The endoscope according to claim 1, wherein the rotating member has an engaging projection, and wherein the cap has an engaging groove with which the engaging projection attachably and detachably engages and which is switchable between a locked position where release of a mounted state between the rotating member and the cap is prevented by engaging the engaging projection and the engaging groove with each other and an unlocked position where the release of the mounted state between the rotating member and the cap is allowed by releasing the engagement between the engaging projection and the engaging groove.

7. The endoscope according to claim 1,
   wherein the engaging part has an engaging piece provided on the proximal end side of the erection operating wire, and
   wherein the engaged part has an engaging recess with which the engaging piece engages, and an engaging claw which is disposed at least on one side of both sides of the engaging recess and with which the erection operating wire engages.

8. The endoscope according to claim 1,
   wherein the engaging part has an engaging piece provided on the proximal end side of the erection operating wire, and
   wherein the engaged part has an engaging recess with which the engaging piece engages, a restricting part that restricts the engaging piece from slipping out in a direction parallel to the rotational axis from the engaging recess, and an opening part that is continuously connected to the engaging recess for attachably and detachably engaging the engaging piece with the engaging recess.

9. The endoscope according to claim 8, further comprising:
   an engaging piece holding member that is provided on the proximal end side of the erection operating wire and holds the engaging piece,
   wherein the engaging piece is disposed at a position offset in a direction orthogonal to an axial direction of the erection operating wire from the erection operating wire.

10. The endoscope according to claim 1,
    wherein the rotating member is provided on a distal end side of the operating part, from the angle knobs.

11. An endoscope comprising:
    an operating part that is provided with an operating member;
    an insertion part that is provided on a distal end side of the operating part and is inserted into a subject;
    an elevator that is provided at a distal end part of the insertion part;
    an erection operating wire that is disposed to be inserted into a wire insertion passage formed from the operating part to the insertion part so as to be movable forward and backward and is attachably and detachably coupled to the elevator on a distal end side thereof;
    an opening that is provided at a proximal end of the wire insertion passage and delivers a proximal end side of the erection operating wire to an outside of the operating part;

a rotating member, comprising a surface, that is disposed to be exposed to the outside of the operating part and is configured to be rotatable around a rotational axis having a component in a direction orthogonal to a longitudinal direction of the operating part depending on the operation of the operating member;

an engaged part that is provided in the rotating member;

an engaging part that is provided on the proximal end side of the erection operating wire and is engageably and disengageably engageable with the engaged part; and a cap that is attachably and detachably mountable on the rotating member and maintains an engaged state between the engaged part and the engaging part by abutting against the erection operating wire to apply a tension.

12. The endoscope according to claim 11, wherein the rotating member has an engaging projection, and wherein the cap member has an engaging groove with which the engaging projection attachably and detachably engages and which is switchable between a locked position where release of a mounted state between the rotating member and the cap member is prevented by engaging the engaging projection and the engaging groove with each other and an unlocked position where the release of the mounted state between the rotating member and the cap member is allowed by releasing the engagement between the engaging projection and the engaging groove.

* * * * *